United States Patent [19]

Okubo et al.

[11] Patent Number: 5,407,950
[45] Date of Patent: Apr. 18, 1995

[54] ARYLALKANOYLAMINE DERIVATIVE AND DRUG CONTAINING THE SAME

[75] Inventors: Akihiro Okubo; Hiroyasu Nishioka; Heihachiro Arai; Yoshiaki Tanaka; Hisayoshi Kato; Naoki Nakata, all of Saitama, Japan

[73] Assignee: Zeria Pharmaceutical Co., Ltd., Tokyo, Japan

[21] Appl. No.: 952,499

[22] PCT Filed: Jun. 7, 1991

[86] PCT No.: PCT/JP91/00771
§ 371 Date: Dec. 7, 1992
§ 102(e) Date: Dec. 7, 1992

[87] PCT Pub. No.: WO91/18877
PCT Pub. Date: Dec. 12, 1991

[30] Foreign Application Priority Data

Jun. 7, 1990 [JP] Japan .................. 2-147281

[51] Int. Cl.⁶ .................. C07D 407/06; C07D 403/06; A61K 31/40; A61K 31/425
[52] U.S. Cl. .................. 514/365; 514/422; 548/200; 548/518
[58] Field of Search .......... 548/200, 518; 514/365, 514/422

[56] References Cited

U.S. PATENT DOCUMENTS 5,028,604  7/1991  Torizuka ............ 514/227.8
5,212,191  5/1993  Toda ................ 514/365

FOREIGN PATENT DOCUMENTS 0201741  11/1986  European Pat. Off.
0303434   2/1989  European Pat. Off.
0321956   6/1989  European Pat. Off.
0345428  12/1989  European Pat. Off.
0372484   6/1990  European Pat. Off.
63-258852 10/1988  Japan.
64-6263    1/1989  Japan.
64-42475   2/1989  Japan.
9012005   10/1990  WIPO.

*Primary Examiner*—Robert Gerstl
*Attorney, Agent, or Firm*—Bacon & Thomas

[57] ABSTRACT

Arylalkanoylamine derivatives having excellent prolyl endopeptidase inhibitory action and resistances to hypoxia and amnesia which are represented by the following general formula (I):

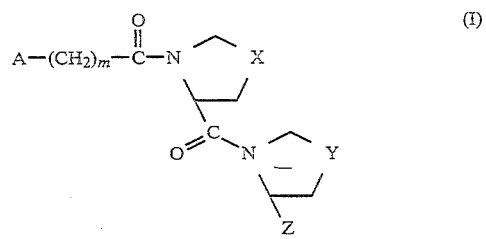

wherein A represents an indanyl, indenyl, 1,2,3,4-tetrahydronaphthalenyl or benzofuranyl group; m represents an integer of 0 to 5; Z represents a hydroxymethyl, formyl, nitrile, hydroxyiminomethyl, semicarbazonomethyl or dialkoxymethyl group; X and Y may be the same or different, and individually represent a methylene group or sulfur atom, wherein compounds defined by the following substituents are excluded: A represents an indanyl, indenyl, or 1,2,3,4-tetrahydronaphthalenyl group; X and Y each represent a methylene group; and Z represents a hydroxymethyl or formyl group. Also disclosed is a pharmaceutical composition and method for improving mneme, cerebral circulation and cerebral metabolism comprising the arylalkanoylamine derivatives as the effective ingredient.

12 Claims, 1 Drawing Sheet

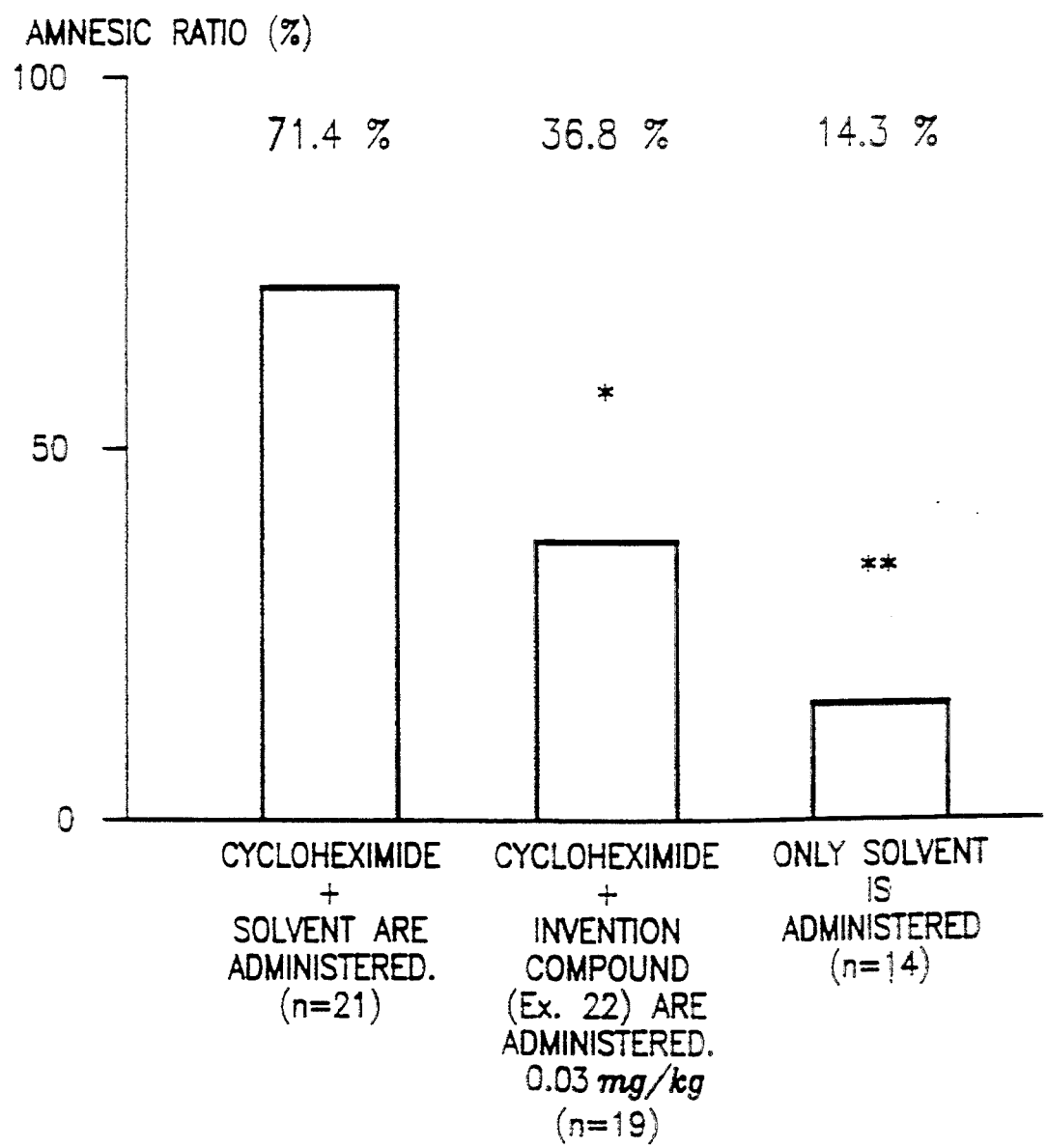

ARYLALKANOYLAMINE DERIVATIVE AND DRUG CONTAINING THE SAME

TECHNICAL FIELD

The present invention relates to a novel arylalkanoylamine derivative having a prolyl endopeptidase inhibitory action and resistances to hypoxia and amnesia, and a drug for improving mneme, cerebral circulation and cerebral metabolism.

BACKGROUND ART

Senile dementia caused by such cerebral disorders as cerebrovascular disorder, cerebral circulation disorder, cerebral metabolism disorder and memory disturbance has become a social problem in the society with prolonged life-span. Development of drugs useful for improving mneme, cerebral circulation and cerebral metabolism are thus desired. A recent clinical report [M. F. Mazurek et al., Neurology, 36, 1133(1986)] revealed a remarkable decrease of peptides participating in mneme or neurotransmission in brains of senile dementia patients.

Prolyl endopeptidase is an enzyme degrading peptides containing proline, and inactivates vasopressin, thyrotropin releasing hormone, neurotensin and the like, responsible for mneme and neurotransmission, which has propagated mneme and learning tests on the inhibitors of the enzyme. It is known that a compound inhibiting prolyl endopeptidase has resistance to amnesia (Japanese Patent Unexamined Publication No. 62-201877; Japanese Pharmacological Journal, Minanisato, et al., 89, 323(1987); ibid, Taira, et al., 89, 243(1987)).

Drugs improving cerebral circulation, cerebral vasodilators, cerebral metabolism accelerators, and the like are clinically used as drugs for treating cerebrovascular disorders. These drugs, however, exhibit only insufficient improvement in neurological symptoms or inability of daily life in the patients, even though they are recognized to improve subjective symptoms.

Therefore, a drug has been expected which has an action for improving cerebral circulation and cerebral metabolism in combination with an action for improving neurological disorders, such as resistance to amnesia and the like, and an action for improving disorders of movements in daily life.

Thus, the present inventors have made various investigations for research of a compound having a prolyl endopeptidase inhibitory action and an action of improving cerebral metabolism, and have synthesized an imide derivative of amino acid, having resistance to amnesia. The inventors have submitted a patent application (Japanese Patent Unexamined Publication No. 1-2503070). Further research works have been continued thereafter so as to make intensive investigations to generate a novel drug for improving mneme, cerebral circulation and brain metabolism, which drug has an excellent prolyl endopeptidase inhibitory action in combination with an action for improving cerebral circulation and cerebral metabolism. Thus, the present invention has been achieved.

DISCLOSURE OF THE INVENTION

The present invention is to provide an arylalkanoylamine derivative represented by the following general formula (I):

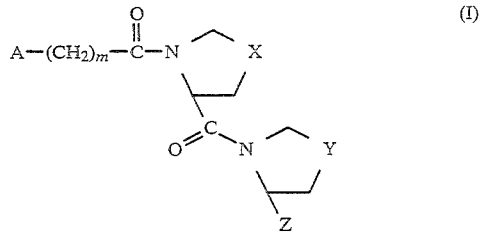

(wherein A represents an indanyl, indenyl group, 1,2,3,4-tetrahydronaphthalenyl or benzofuranyl group; m represents an integer of 0 to 5; Z represents a hydroxymethyl, formyl, nitrile, hydroxyiminomethyl, semicarbazonomethyl or dialkoxymethyl group; X and Y may be the same or different, and individually represent methylene group or sulfur atom, provided that the case wherein A represents an indanyl, indenyl, or 1,2,3,4-tetrahydronaphthalenyl group; X and Y both represent a methylene group; Z represents a hydroxymethyl or formyl group, is excluded. Also disclosed is a pharmaceutical composition for improving mneme, cerebral circulation and cerebral metabolism comprising the arylalkanoylamine derivate as an effective ingredient.

BRIEF DESCRIPTION OF DRAWINGS

FIG. 1 is a view depicting the resistance to amnesia of the compound (I) of the present invention. The ordinate represents an amnesic ratio.

BEST MODE FOR CARRYING OUT THE INVENTION

In the general formula (I) representing the compound of the present invention, specific examples of indanyl group, indenyl group, 1,2,3,4-tetrahydronaphthalenyl group and benzofuranyl group are illustrated by indan-1-yl group, indan-2-yl group, inden-1-yl group, inden-2-yl group, 1,2,3,4-tetrahydronaphthalen-1-yl group, 1,2,3,4-tetrahydronaphthalen-2-yl group, benzofuran-2-yl group, benzofuran-3-yl group and the like. The dialkoxymethyl group as Z includes dimethoxymethyl group, diethoxymethyl group and the like. An integer of 0 to 5, and preferably an integer of 0 to 3 in particular are represented by m.

The compound (I) of the present invention contains two or three asymmetric carbons, and in accordance with the present invention, the steric configuration of the substituents on the individual asymmetric carbons may satisfactorily be either R or S or a mixture of R and S.

Representative examples of the compound (I) of the present invention are illustrated as follows.
1-[3-(indan-2-ylcarbonyl)-L-thioprolyl]-L-prolinol
1-[3-(indan-2-ylacetyl)-L-thioprolyl]-L-prolinol
1-[3-[3-(indan-2-yl)propanoyl]-L-thioprolyl]-L-prolinol
1-[3-[4-(indan-2-yl)butanoyl]-L-thioprolyl]-L-prolinol
1-[3-[6-(indan-2-yl)hexanoyl]-L-thioprolyl]-L-prolinol
3-[1-(indan-2-ylcarbonyl)-L-prolyl]-L-prolinol
3-[1-(indan-2-ylacetyl)-L-prolyl]-L-thioprolinol
3-[1-[3-(indan-2-yl)propanoyl]-L-prolyl]-L-thioprolinol
3-[1-[4-(indan-2-yl)butanoyl]-L-prolyl]-L-thioprolinol
3-[1-[5-(indan-2-yl)pentanoyl]-L-prolyl]-L-thioprolinol
3-[3-(indan-2-ylcarbonyl)-L-thioprolyl]-L-thioprolinol
3-[3-(indan-2-ylacetyl)-L-thioprolyl]-L-thioprolinol
3-[3-[3-(indan-2-yl)propanoyl]-L-thioprolyl]-L-thioprolinol 3-[3-[4-(indan-2-yl)butanoyl]-L-thioprolyl]-L-thioprolinol
3-[3-[6-(indan-2-yl)hexanoyl]-L-thioprolyl]-L-thioprolinol
1-[3-(inden-2-ylcarbonyl)-L-thioprolyl]-L-prolinol
1-[3-(inden-2-ylacetyl)-L-thioprolyl]-L-prolinol
1-[3-[3-(inden-2-yl)propanoyl]-L-thioprolyl]-L-prolinol
1-[3-[4-(inden-2-yl)butanoyl]-L-thioprolyl]-L-prolinol
1-[3-[5-(inden-2-yl)pentanoyl]-L-thioprolyl]-L-prolinol
3-[1-(inden-2-ylcarbonyl)-L-prolyl]-L-thioprolinol
3-[1-(inden-2-ylacetyl)-L-prolyl]-L-thioprolinol
3-[1-[3-(inden-2-yl)propanoyl]-L-prolyl]-L-thioprolinol
3-[1-[4-(inden-2-yl)butanoyl]-L-prolyl]-L-thioprolinol
3-[1-[5-(inden-2-yl)pentanoyl]-L-prolyl]-L-thioprolinol
3-[1-[6-(inden-2-yl)hexanoyl]-L-prolyl]-L-thioprolinol
3-[3-(inden-2-ylcarbonyl)-L-thioprolyl]-L-thioprolinol
3-[3-(inden-2-ylacetyl)-L-thioprolyl]-L-thioprolinol
3-[3-[3-(inden-2-yl)propanoyl]-L-thioprolyl]-L-thioprolinol
3-[3-[4-(inden-2-yl)butanoyl]-L-thioprolyl]-L-thioprolinol
3-[3-[5-(inden-2-yl)pentanoyl]-L-thioprolyl]-L-thioprolinol
1-[3-((S)-1,2,3,4-tetrahydronaphthalen-2-ylcarbonyl)-L-thioprolyl]-L-prolinol
1-[3-((S)-1,2,3,4-tetrahydronaphthalen-2-ylacetyl)-L-thioprolyl]-L-prolinol
1-[3-[3-((S)-1,2,3,4-tetrahydronaphthalen-2-yl)pentanoyl]-L-thioprolyl]-L-prolinol
1-[3-[4-((S)-1,2,3,4-tetrahydronaphthalenyl-2-yl)butanoyl]-L-thioprolyl]-L-prolinol
1-[3-[5-((S)-1,2,3,4-tetrahydronaphthalen-2-yl)pentanoyl]-L-thioprolyl]-L-prolinol
3-[1-((S)-1,2,3,4-tetrahydronaphthalen-2-ylcarbonyl)-L-prolyl]-L-thioprolinol
3-[1-((S)-1,2,3,4-tetrahydronaphthalen-2-ylacetyl)-L-prolyl]-L-thioprolinol
3-[1-[3-((S)-1,2,3,4-tetrahydronaphthalen-2-yl)propanoyl]-L-prolyl]-L-thioprolinol
3-[1-[4-((S)-1,2,3,4-tetrahydronaphthalen-2-yl)butanoyl]-L-prolyl]-L-thioprolinol
3-[3-((S)-1,2,3,4-tetrahydronaphthalen-2-ylcarbonyl)-L-thioprolyl]-L-thioprolinol
3-[3-((S)-1,2,3,4-tetrahydronaphthalen-2-ylacetyl)-L-thioprolyl]-L-thioprolinol
3-[3-[3-((S)-1,2,3,4-tetrahydronaphthalen-2-yl)propanoyl]-L-thioprolyl]-L-thioprolinol
3-[3-[4-((S)-1,2,3,4-tetrahydronaphthalen-2-yl)butanoyl]-L-thioprolyl]-L-thioprolinol
1-[3-((R)-1,2,3,4-tetrahydronaphthalen-2-ylcarbonyl)-L-thioprolyl]-L-prolinol
1-[3-((R)-1,2,3,4-tetrahydronaphthalen-2-ylacetyl)-L-thioprolyl]-L-prolinol
1-[3-[3-((R)-1,2,3,4-tetrahydronaphthalen-2-yl)propanoyl]-L-thioprolyl]-L-prolinol
1-[3-[4-((R)-1,2,3,4-tetrahydronaphthalen-2-yl)butanoyl]-L-thioprolyl]-L-prolinol
1-[3-[5-((R)-1,2,3,4-tetrahydronaphthalen-2-yl)pentanoyl]-L-thioprolyl]-L-prolinol
3-[1-((R)-1,2,3,4-tetrahydronaphthalen-2-ylcarbonyl)-L-prolyl]-L-thioprolinol
3-[1-((R)-1,2,3,4-tetrahydronaphthalen-2-ylacetyl)-L-prolyl]-L-thioprolinol
3-[1-[3-((R)-1,2,3,4-tetrahydronaphthalen-2-yl)propanoyl]-L-prolyl]-L-thioprolinol
3-[1-[4-((R)-1,2,3,4-tetrahydronaphthalen-2-yl)butanoyl]-L-prolyl]-L-thioprolinol
3-[3-((R)-1,2,3,4-tetrahydronaphthalen-2-ylcarbonyl)-L-thioprolyl]-L-thioprolinol
3-[3-((R)-1,2,3,4-tetrahydronaphthalen-2-ylacetyl)-L-thioprolyl]-L-thioprolinol
3-[3-[3-((R)-1,2,3,4-tetrahydronaphthalen-2-yl)propanoyl]-L-thioprolyl]-L-thioprolinol
3-[3-[4-((R)-1,2,3,4-tetrahydronaphthalen-2-yl)butanoyl]-L-thioprolyl]-L-thioprolinol
3-[3-[6-((R)-1,2,3,4-tetrahydronaphthalen-2-yl)hexanoyl]-L-thioprolyl]-L-thioprolinol
1-[1-(benzofuran-2-ylcarbonyl)-L-prolyl]-L-prolinol
1-[1-(benzofuran-2-ylacetyl)-L-prolyl]-L-prolinol
1-[1-[3-(benzofuran-2-yl)propanoyl]-L-prolyl]-L-prolinol
1-[1-[4-(benzofuran-2-yl)butanoyl]-L-prolyl]-L-prolinol
1-[3-(benzofuran-2-ylcarbonyl)-L-thioprolyl]-L-prolinol
1-[3-(benzofuran-2-ylacetyl)-L-thioprolyl]-L-prolinol
1-[3-[3-(benzofuran-2-yl)propanoyl]-L-thioprolyl]-L-prolinol
1-[3-[4-(benzofuran-2-yl)butanoyl]-L-thioprolyl]-L-prolinol
1-[3-[5-(benzofuran-2-yl)pentanoyl]-L-thioprolyl]-L-prolinol
3-[1-(benzofuran-2-ylcarbonyl)-L-prolyl]-L-thioprolinol
3-[1-(benzofuran-2-ylacetyl)-L-prolyl]-L-thioprolinol
3-[1-[3-(benzofuran-2-yl)propanoyl]-L-prolyl]-L-thioprolinol
3-[1-[4-(benzofuran-2-yl)butanoyl]-L-prolyl]-L-thioprolinol
3-[1-[5-(benzofuran-2-yl)pentanoyl]-L-prolyl]-L-thioprolinol
3-[3-(benzofuran-2-ylcarbonyl)-L-thioprolyl]-L-thioprolinol
3-[3-(benzofuran-2-ylacetyl)-L-thioprolyl]-L-thioprolinol
3-[3-[3-(benzofuran-2-yl)propanoyl]-L-thioprolyl]-L-thioprolinol
3-[3-[4-(benzofuran-2-yl)butanoyl]-L-thioprolyl]-L-thioprolinol
3-[3-[5-(benzofuran-2-yl)pentanoyl]-L-thioprolyl]-L-thioprolinol
1-[3-(indan-2-ylcarbonyl)-L-thioprolyl]-L-prolinal
1-[3-(indan-2-ylacetyl)-L-thioprolyl]-L-prolinal
1-[3-[3-(indan-2-yl)propanoyl]-L-thioprolyl]-L-prolinal
1-[3-[4-(indan-2-yl)butanoyl]-L-thioprolyl]-L-prolinal
1-[3-[6-(indan-2-yl)hexanoyl]-L-thioprolyl]-L-prolinal
3-[1-(indan-2-ylcarbonyl)-L-prolyl]-L-thioprolinal
3-[1-(indan-2-ylacetyl)-L-prolyl]-L-thioprolinal
3-[1-[3-(indan-2-yl)propanoyl]-L-prolyl]-L-thioprolinal
3-[1-[4-(indan-2-yl)butanoyl]-L-prolyl]-L-thioprolinal
3-[1-[5-(indan-2-yl)pentanoyl]-L-prolyl]-L-thioprolinal
3-[3-(indan-2-ylcarbonyl)-L-thioprolyl]-L-thioprolinal
3-[3-(indan-2-ylacetyl)-L-thioprolyl]-L-thioprolinal
3-[3-[3-(indan-2-yl)propanoyl]-L-thioprolyl]-L-thioprolinal
3-[3-[4-(indan-2-yl)butanoyl]-L-thioprolyl]-L-thioprolinal
3-[3-[6-(indan-2-yl)hexanoyl]-L-thioprolyl]-L-thioprolinal
1-[3-(inden-2-ylcarbonyl)-L-thioprolyl]-L-prolinal
1-[3-(inden-2-ylacetyl)-L-thioprolyl]-L-prolinal
1-[3-[3-(inden-2-yl)propanoyl]-L-thioprolyl]-L-prolinal
1-[3-[4-(inden-2-yl)butanoyl]-L-thioprolyl]-L-prolinal
1-[3-[5-(inden-2-yl)pentanoyl]-L-thioprolyl]-L-prolinal
3-[1-(inden-2-ylcarbonyl)-L-prolyl]-L-thioprolinal
3-[1-(inden-2-ylacetyl)-L-prolyl]-L-thioprolinal 3-[1-[3-(inden-2-yl)propanoyl]-L-prolyl]-L-thioprolinal
3-[1-[4-(inden-2-yl)butanoyl]-L-prolyl]-L-thioprolinal
3-[1-[5-(inden-2-yl)pentanoyl]-L-prolyl]-L-thioprolinal
3-[1-[6-(inden-2-yl)hexanoyl]-L-prolyl]-L-thioprolinal
3-[3-(inden-2-ylcarbonyl)-L-thioprolyl]-L-prolinal
3-[3-(inden-2-ylacetyl)-L-thioprolyl]-L-prolinal
3-[3-[3-(inden-2-yl)propanoyl]-L-thioprolyl]-L-prolinal
3-[3-[4-(inden-2-yl)butanoyl]-L-thioprolyl]-L-prolinal
3-[3-[5-(inden-2-yl)pentanoyl]-L-thioprolyl]-L-prolinal
1-[3-((S)-1,2,3,4-tetrahydronaphthalen-2-ylcarbonyl)-L-thioprolyl]-L-prolinal
1-[3-((S)-1,2,3,4-tetrahydronaphthalen-2-ylacetyl)-L-thioprolyl]-L-prolinal
1-[3-[3-((S)-1,2,3,4-tetrahydronaphthalen-2-yl)propanoyl]-L-thioprolyl]-L-prolinal
1-[3-[4-((S)-1,2,3,4-tetrahydronaphthalen-2-yl)butanoyl]-L-thioprolyl]-L-prolinal
1-[3-[5-((S)-1,2,3,4-tetrahydronaphthalen-2-yl)pentanoyl]-L-thioprolyl]-L-prolinal
3-[1-((S)-1,2,3,4-tetrahydronaphthalen-2-ylcarbonyl)-L-prolyl]-L-thioprolinal
3-[1-((S)-1,2,3,4-tetrahydronaphthalen-2-ylacetyl)-L-prolyl]-L-thioprolinal
3-[1-[3-((S)-1,2,3,4-tetrahydronaphthalen-2-yl)propanoyl]-L-prolyl]-L-thioprolinal
3-[1-[4-((S)-1,2,3,4-tetrahydronaphthalen-2-yl)butanoyl]-L-prolyl]-L-thioprolinal
3-[3-((S)-1,2,3,4-tetrahydronaphthalen-2-ylcarbonyl)-L-thioprolyl]-L-thioprolinal
3-[3-((S)-1,2,3,4-tetrahydronaphthalen-2-ylacetyl)-L-thioprolyl]-L-thioprolinal
3-[3-[3-((S)-1,2,3,4-tetrahydronaphthalen-2-yl)propanoyl]-L-thioprolyl]-L-thioprolinal
3-[3-[4-((S)-1,2,3,4-tetrahydronaphthalen-2-yl)butanoyl]-L-thioprolyl]-L-thioprolinal
1-[3-((R)-1,2,3,4-tetrahydronaphthalen-2-ylcarbonyl)-L-thioprolyl]-L-prolinal
1-[3-((R)-1,2,3,4-tetrahydronaphthalen-2-ylacetyl)-L-thioprolyl]-L-prolinal
1-[3-[3-((R)-1,2,3,4-tetrahydronaphthalen-2-yl)propanoyl]-L-thioprolyl]-L-prolinal
1-[3-[4-((R)-1,2,3,4-tetrahydronaphthalen-2-yl)butanoyl]-L-thioprolyl]-L-prolinal
1-[3-[5-((R)-1,2,3,4-tetrahydronaphthalen-2-yl)pentanoyl]-L-thioprolyl]-L-prolinal
3-[1-((R)-1,2,3,4-tetrahydronaphthalen-2-ylcarbonyl)-L-propyl-L-thioprolinal
3-[1-((R)-1,2,3,4-tetrahydronaphthalen-2-ylacetyl)-L-prolyl]-L-thioprolinal
3-[1-[3-((R)-1,2,3,4-tetrahydronaphthalen-2-yl)propanoyl]-L-prolyl]-L-thioprolinal
3-[1-[4-((R)-1,2,3,4-tetrahydronaphthalen-2-yl)butanoyl]-L-prolyl]-L-thioprolinal
3-[3-((R)-1,2,3,4-tetrahydronaphthalen-2-ylcarbonyl)-L-thioprolyl]-L-thioprolinal
3-[3-((R)-1,2,3,4-tetrahydronaphthalen-2-ylacetyl)-L-thioprolyl]-L-thioprolinal
3-[3-[3-((R)-1,2,3,4-tetrahydronaphthalen-2-yl)propanol]-L-thioprolyl]-L-thioprolinal
3-[3-[4-((R)-1,2,3,4-tetrahydronaphthalen-2-yl)butanoyl]-L-thioprolyl]-L-thioprolinal
3-[3-[6-((R)-1,2,3,4-tetrahydronaphthalen-2-yl)hexanoyl]-L-thioprolyl]-L-thioprolinal
1-[1-(benzofuran-2-ylcarbonyl)-L-prolyl]-L-prolinal
1-[1-(benzofuran-2-ylacetyl)-L-prolyl]-L-prolinal
1-[1-[3-(benzofuran-2-yl)propanoyl]-L-propyl]-L-prolinal
1-[1-[4-(benzofuran-2-yl)butanoyl]-L-propyl]-L-prolinal
1-[3-(benzofuran-2-ylcarbonyl)-L-thioprolyl]-L-prolinal
1-[3-(benzofuran-2-ylacetyl)-L-thioprolyl]-L-prolinal
1-[3-[3-(benzofuran-2-yl)propanoyl]-L-thioprolyl]-L-prolinal
1-[3-[4-(benzofuran-2-yl)butanoyl]-L-thioprolyl]-L-prolinal
1-[3-[5-(benzofuran-2-yl)pentanoyl]-L-thioprolyl]-L-prolinal
3-[1-(benzofuran-2-ylcarbonyl)-L-prolyl]-L-prolinal
3-[1-(benzofuran-2-ylacetyl)-L-prolyl]-L-prolinal
3-[1-[3-(benzofuran-2-yl)propanoyl]-L-prolyl]-L-prolinal
3-[1-[4-(benzofuran-2-yl)butanoyl]-L-prolyl]-L-prolinal
3-[1-[5-(benzofuran-2-yl)pentanoyl]-L-prolyl]-L-prolinal
3-[3-(benzofuran-2-ylcarbonyl)-L-thioprolyl]-L-thioprolinal
3-[3-(benzofuran-2-ylacetyl)-L-thioprolyl]-L-thioprolinal
3-[3-[3-(benzofuran-2-yl)propanoyl]-L-thioprolyl]-L-thioprolinal
3-[3-[4-(benzofuran-2-yl)butanoyl]-L-thioprolyl]-L-thioprolinal
3-[3-[5-(benzofuran-2-yl)pentanoyl]-L-thioprolyl]-L-thioprolinal
(2S)-1-[1-(indan-2-ylcarbonyl)-L-prolyl]-2-pyrrolidine aldoxime
(2S)-1-[1-(indan-2-ylacetyl)-L-prolyl]-2-pyrrolidine aldoxime
(2S)-1-[1-[3-(indan-2-yl)propanoyl]-L-prolyl]-2-pyrrolidine aldoxime
(2S)-1-[1-[4-(indan-2-yl)butanoyl]-L-prolyl]-2-pyrrolidine aldoxime
(4R)-3-[1-(indan-2-ylcarbonyl)-L-prolyl]-4-thiazolidine aldoxime
(4R)-3-[1-(indan-2-ylacetyl)-L-prolyl]-4-thiazolidine aldoxime
(4R)-[1-[3-(indan-2-yl)propanoyl]-L-prolyl]-4-thiazolidine aldoxime
(4R)-3-[1-[4-(indan-2-yl)butanoyl]-L-prolyl]-4-thiazolidine aldoxime
(2S)-1-[3-(indan-2-ylcarbonyl)-L-thioprolyl]-2-pyrrolidine aldoxime
(2S)-1-[3-(indan-2-ylacetyl)-L-thioprolyl]-2-pyrrolidine aldoxime
(2S)-1-[3-[3-(indan-2-yl)propanoyl]-L-thioprolyl]-2-pyrrolidine aldoxime
(2S)-1-[3-[3-(indan-2-yl)butanoyl]-L-thioprolyl-2-pyrrolidine aldoxime aldoxime
(4R)-3-[3-(indan-2-ylcarbonyl)-L-thioprolyl]-4-thiazolidine aldoxime
(4R)-3-[3-(indan-2-ylacetyl)-L-thioprolyl]-4-thiazolidine aldoxime
(4R)-3-[3-[3-(indan-2-yl)propanoyl]-L-thioprolyl]-4-thiazolidine aldoxime
(4R)-3-[3-[4-(indan-2-yl)butanoyl]-L-thioprolyl]-4-thiazolidine aldoxime
(2S)-1-[1-(indan-2-ylcarbonyl)-L-prolyl]-2-cyanopyrrolidine
(2S)-1-[1-(indan-2-ylacetyl)-L-prolyl]-2-cyanopyrrolidine
(2S)-1-[1-[3-(indan-2-yl)propanoyl]-L-prolyl]-2-cyanopyrrolidine
(2S)-1-[1-[4-(indan-2-yl)butanoyl]-L-prolyl]-2-cyanopyrrolidine (4R)-3-[1-(indan-2-ylcarbonyl)-L-prolyl]-4-cyano-thiazolidine
(4R)-3-[1-(indan-2-ylacetyl)-L-prolyl]-4-cyanothiazolidine
(4R)-3-[1-[3-(indan-2-yl)propanoyl]-L-prolyl]-4-cyano-thiazolidine
(4R)-3-[1-[4-(indan-2-yl)butanoyl]-L-prolyl]-4-cyano-thiazolidine
(2S)-1-[3-(indan-2-ylcarbonyl)-L-thioprolyl]-2-cyanopyrrolidine
(2S)-1-[3-(indan-2-ylacetyl)-L-thioprolyl]-2-cyanopyrrolidine
(2S)-1-[3-[3-(indan-2-yl)propanoyl]-L-thioprolyl]-2-cyanopyrrolidine
(2S)-1-[3-[4-(indan-2-yl)butanoyl]-L-thioprolyl]-2-cyanopyrrolidine
(4R)-3-[3-(indan-2-ylcarbonyl)-L-thioprolyl]-4-cyano-thiazolidine
(4R)-3-[3-(indan-2-ylacetyl)-L-thioprolyl]-4-cyano-thiazolidine
(4R)-3-[3-[3-(indan-2-yl)propanoyl]-L-thioprolyl]-4-cyanothiazolidine
(4R)-3-[3-[4-(indan-2-yl)butanoyl]-L-thioprolyl]-4-cyanothiazolidine
(2S)-1-[1-(indan-2-ylcarbonyl)-L-prolyl]-2-pyrrolidine carbaldehyde dimethyl acetal
(2S)-1-[1-(indan-2-ylacetyl)-L-prolyl]-2-pyrrolidine carbaldehyde dimethyl acetal
(2S)-1-[1-[3-(indan-2-yl)propanoyl]-L-prolyl]-2-pyrrolidine carbaldehyde dimethyl acetal
(4R)-3-[1-(indan-2-ylcarbonyl)-L-prolyl]-4-thiazolidine carbaldehyde dimethyl acetal
(4R)-3-[1-(indan-2-ylacetyl)-L-prolyl]-4-thiazolidine carbaldehyde dimethyl acetal
(4R)-3-[1-[3-(indan-2-yl)propanoyl]-L-prolyl]-4-thiazolidine carbaldehyde dimethyl acetal
(2S)-1-[3-(indan-2-ylcarbonyl)-L-thioprolyl]-2-pyrrolidine carbaldehyde dimethyl acetal
(2S)-1-[3-(indan-2-ylacetyl)-L-thioprolyl]-2-pyrrolidine carbaldehyde dimethyl acetal
(2S)-1-[3-[3-(indan-2-yl)propanoyl]-L-thioprolyl]-2-pyrrolidine carbaldehyde dimethyl acetal
(4R)-3-[3-(indan-2-ylcarbonyl)-L-thioprolyl]-4-thiazolidine carbaldehyde dimethyl acetal
(4R)-3-[3-(indan-2-ylacetyl)-L-thioprolyl]-4-thiazolidine carbaldehyde dimethyl acetal
(4R)-3-[3-[3-(indan-2-yl)propanoyl]-L-thioprolyl]-4-thiazolidine carbaldehyde dimethyl acetal
(2S)-1-[1-(indan-2-ylcarbonyl)-L-prolyl]-2-pyrrolidine carbaldehyde diethyl acetal
(2S)-1-[1-(indan-2-ylacetyl)-L-prolyl]-2-pyrrolidine carbaldehyde diethyl acetal
(2S)-1-[1-[3-(indan-2-yl)propanoyl]-L-prolyl]-2-pyrrolidine carbaldehyde diethyl acetal
(4R)-3-[1-(indan-2-ylcarbonyl)-L-prolyl]-4-thiazolidine carbaldehyde diethyl acetal
(4R)-3-[1-(indan-2-ylacetyl)-L-prolyl]-4-thiazolidine carbaldehyde diethyl acetal
(4R)-3-[1-[3-(indan-2-yl)propanoyl]-L-prolyl]-4-thiazolidine carbaldehyde diethyl acetal
(2S)-1-[3-(indan-2-ylcarbonyl)-L-thioprolyl]-2-pyrrolidine carbaldehyde diethyl acetal
(2S)-1-[3-(indan-2-ylacetyl)-L-thioprolyl]-2-pyrrolidine carbaldehyde diethyl acetal
(2S)-1-[3-[3-(indan-2-yl)propanoyl]-L-thioprolyl]-2-pyrrolidine carbaldehyde diethyl acetal
(4R)-3-[3-(indan-2-ylcarbonyl)-L-thioprolyl]-4-thiazolidine carbaldehyde diethyl acetal
(4R)-3-[3-(indan-2-ylacetyl)-L-thioprolyl]-4-thiazolidine carbaldehyde diethyl acetal
(4R)-3-[3-[3-(indan-2-yl)propanoyl]-L-thioprolyl]-4-thiazolidine carbaldehyde diethyl acetal
(2S)-1-[1-(indan-2-ylcarbonyl)-L-prolyl]-2-pyrrolidine carbaldehyde semicarbazone
(2S)-1-[1-(indan-2-ylacetyl)-L-prolyl]-2-pyrrolidine carbaldehyde semicarbazone
(2S)-1-[1-[3-(indan-2-yl)propanoyl]-L-prolyl]-2-pyrrolidine carbaldehyde semicarbazone
(4R)-3-[1-(indan-2-ylcarbonyl)-L-prolyl]-4-thiazolidine carbaldehyde semicarbazone
(4R)-3-[1-(indan-2-ylacetyl)-L-prolyl]-4-thiazolidine carbaldehyde semicarbazone
(4R)-3-[1-[3-(indan-2-yl)propanoyl]-L-prolyl]-4-thiazolidine carbaldehyde semicarbazone
(2S)-1-[3-(indan-2-ylcarbonyl)-L-thioprolyl]-2-pyrrolidine carbaldehyde semicarbazone
(2S)-1-[3-(indan-2-ylacetyl)-L-thioprolyl]-2-pyrrolidine carbaldehyde semicarbazone
(2S)-1-[3-[3-(indan-2-yl)propanoyl]-L-thioprolyl]-2-pyrrolidine carbaldehyde semicarbazone
(4R)-3-[3-(indan-2-ylcarbonyl)-L-thioprolyl]-4-thiazolidine carbaldehyde semicarbazone
(4R)-3-[3-(indan-2-ylacetyl)-L-thioprolyl]-4-thiazolidine carbaldehyde semicarbazone
(4R)-3-[3-[3-(indan-2-yl)propanoyl]-L-thioprolyl]-4-thiazolidine carbaldehyde semicarbazone
(2S)-1-[1-((S)-1,2,3,4-tetrahydronaphthalen-2-ylcarbonyl)-L-prolyl]-2-pyrrolidine aldoxime
(2S)-1-[1-((S)-1,2,3,4-tetrahydronaphthalen-2-ylacetyl)-L-prolyl]-2-pyrrolidine aldoxime
(2S)-1-[1-[3-((S)-1,2,3,4-tetrahydronaphthalen-2-yl)propanoyl]-L-prolyl]-2-pyrrolidine aldoxime
(4R)-3-[1-((S)-1,2,3,4-tetrahydronaphthalen-2-ylcarbonyl)-L-prolyl]-4-thiazolidine aldoxime
(4R)-3-[1-((S)-1,2,3,4-tetrahydronaphthalen-2-ylacetyl)-L-prolyl]-4-thiazolidine aldoxime
(4R)-3-[1-[3-((S)-1,2,3,4-tetrahydronaphthalen-2-yl)propanoyl]-L-prolyl]-4-thiazolidine aldoxime
(2S)-1-[3-((S)-1,2,3,4-tetrahydronaphthalen-2-ylcarbonyl)-L-thioprolyl]-2-pyrrolidine aldoxime
(2S)-1-[3-((S)-1,2,3,4-tetrahydronaphthalen-2-ylacetyl)-L-thioprolyl]-2-pyrrolidine aldoxime
(2S)-1-[3-[3-((S)-1,2,3,4-tetrahydronaphthalen-2-yl)propanoyl]-L-thioprolyl]-2-pyrrolidine aldoxime
(4R)-3-[3-((S)-1,2,3,4-tetrahydronaphthalen-2-ylcarbonyl)-L-thioprolyl]-4-thiazolidine aldoxime
(4R)-3-[3-((S)-1,2,3,4-tetrahydronaphthalene-2-ylacetyl)-L-thioprolyl]-4-thiazolidine aldoxime
(4R)-3-[3-[3-((S)-1,2,3,4-tetrahydronaphthalen-2-yl)propanoyl]-L-thioprolyl]-4-thiazolidine aldoxime
(2S)-1-[1-((S)-1,2,3,4-tetrahydronaphthalen-2-ylcarbonyl)-L-prolyl]-2-cyanopyrrolidine
(2S)-1-[1-((S)-1,2,3,4-tetrahydronaphthalen-2-ylacetyl)-L-prolyl]-2-cyanopyrrolidine
(2S)-1-[1-[3-((S)-1,2,3,4-tetrahydronaphthalen-2-yl)propanoyl]-L-prolyl]-2-cyanopyrrolidine
(4R)-3-[1-((S)-1,2,3,4-tetrahydronaphthalen-2-ylcarbonyl)-L-prolyl]-4-cyanothiazolidine
(4R)-3-[1-((S)-1,2,3,4-tetrahydronaphthalen-2-ylacetyl)-L-prolyl]-4-cyanothiazolidine
(4R)-3-[1-[3-((S)-1,2,3,4-tetrahydronaphthalen-2-yl)propanoyl]-L-prolyl]-4-cyanothiazolidine
(2S)-1-[3-((S)-1,2,3,4-tetrahydronaphthalen-2-ylcarbonyl)-L-thioprolyl]-2-cyanopyrrolidine
(2S)-1-[3-((S)-1,2,3,4-tetrahydronaphthalen-2-ylacetyl)-L-thioprolyl]-2-cyanopyrrolidine (2S)-1-[3-[3-((S)-1,2,3,4-tetrahydronaphthalen-2-yl)propanoyl]-L-thioprolyl]-2-cyanopyrrolidine (4R)-3-[3-((S)-1,2,3,4-tetrahydronaphthalen-2-ylcarbonyl)-L-thioprolyl]-4-cyanothiazolidine (4R)-3-[3-((S)-1,2,3,4-tetrahydronaphthalen-2-ylacetyl)-L-thioprolyl]-4-cyanothiazolidine (4R)-3-[3-[3-((S)-1,2,3,4-tetrahydronaphthalen-2-yl)propanoyl]-L-thioprolyl]-4-cyanothiazolidine (2S)-1-[1-((R)-1,2,3,4-tetrahydronaphthalen-2-ylcarbonyl)-L-prolyl]-2-cyanopyrrolidine (2S)-1-[1-((R)-1,2,3,4-tetrahydronaphthalen-2-ylacetyl)-L-prolyl]-2-cyanopyrrolidine (2S)-1-[1-[3-((R)-1,2,3,4-tetrahydronaphthalen-2-yl)propanoyl]-L-prolyl]-2-cyanopyrrolidine (4R)-3-[1-((R)-1,2,3,4-tetrahydronaphthalen-2-ylcarbonyl)-L-prolyl]-4-cyanothiazolidine (4R)-3-[1-((R)-1,2,3,4-tetrahydronaphthalen-2-ylacetyl)-L-prolyl]-4-cyanothiazolidine (4R)-3-[1-[3-((R)-1,2,3,4-tetrahydronaphthalen-2-yl)propanoyl]-L-prolyl]-4-cyanothiazolidine (2S)-1-[3-((R)-1,2,3,4-tetrahydronaphthalen-2-ylcarbonyl)-L-thioprolyl]-2-cyanopyrrolidine (2S)-1-[3-((R)-1,2,3,4-tetrahydronaphthalen-2-ylacetyl)-L-thioprolyl]-2-cyanopyrrolidine (2S)-1-[3-[3-((R)-1,2,3,4-tetrahydronaphthalen-2-yl)propanoyl]-L-thioprolyl]-2-cyanopyrrolidine (4R)-3-[3-((R)-1,2,3,4-tetrahydronaphthalen-2-ylcarbonyl)-L-thioprolyl]-4-cyanothiazolidine (4R)-3-[3-((R)-1,2,3,4-tetrahydronaphthalen-2-ylacetyl)-L-thioprolyl]-4-cyanothiazolidine (4R)-3-[3-[3-((R)-1,2,3,4-tetrahydronaphthalen-2-yl)propanoyl]-L-thioprolyl]-4-cyanothiazolidine (2S)-1-[1-((S)-1,2,3,4-tetrahydronaphthalen-2-ylcarbonyl)-L-prolyl]-2-pyrrolidine carbaldehyde dimethyl acetal (2S)-1-[1-((S)-1,2,3,4-tetrahydronaphthalen-2-ylacetyl)-L-prolyl]-2-pyrrolidine carbaldehyde dimethyl acetal (2S)-1-[1-[3-((S)-1,2,3,4-tetrahydronaphthalen-2-yl)propanoyl]-L-prolyl]-2-pyrrolidine carbaldehyde dimethyl acetal (4R)-3-[1-((S)-1,2,3,4-tetrahydronaphthalen-2-ylcarbonyl)-L-prolyl]-4-thiazolidine carbaldehyde dimethyl acetal (4R)-3-[1-((S)-1,2,3,4-tetrahydronaphthalen-2-ylacetyl)-L-prolyl]-4-thiazolidine carbaldehyde dimethyl acetal (4R)-3-[1-[3-((S)-1,2,3,4-tetrahydronaphthalen-2-yl)propanoyl]-L-prolyl]-4-thiazolidine carbaldehyde dimethyl acetal (2S)-1-[3-((S)-1,2,3,4-tetrahydronaphthalen-2-ylcarbonyl)-L-thioprolyl]-2-pyrrolidine carbaldehyde dimethyl acetal (2S)-1-[3-((S)-1,2,3,4-tetrahydronaphthalen-2-ylacetyl)-L-thioprolyl]-2-pyrrolidine carbaldehyde dimethyl acetal (2S)-1-[3-[3-((S)-1,2,3,4-tetrahydronaphthalene-2-yl propanoyl]-L-thioprolyl]-2-pyrrolidine carbaldehyde dimethyl acetal (4R)-3-[3-((S)-1,2,3,4-tetrahydronaphthalen-2-ylcarbonyl)-L-thioprolyl]-4-thiazolidine carbaldehyde dimethyl acetal (4R)-3-[3-((S)-1,2,3,4-tetrahydronaphthalen-2-ylacetyl)-L-thioprolyl]-4-thiazolidine carbaldehyde dimethyl acetal (4R)-3-[3-[3-((S)-1,2,3,4-tetrahydronaphthalen-2-yl)propanoyl]-L-thioprolyl]-4-thiazolidine carbaldehyde dimethyl acetal (2S)-1-[1-((R)-1,2,3,4-tetrahydronaphthalen-2-ylcarbonyl)-L-prolyl]-2-pyrrolidine carbaldehyde dimethyl acetal (2S)-1-[1-((R)-1,2,3,4-tetrahydronaphthalen-2-ylacetyl)-L-prolyl]-2-pyrrolidine carbaldehyde dimethyl acetal (2S)-1-[1-[3-((R)-1,2,3,4-tetrahydronaphthalen-2-yl)propanoyl]-L-prolyl]-2-pyrrolidine carbaldehyde dimethyl acetal (4R)-3-[1-((R)-1,2,3,4-tetrahydronaphthalen-2-ylcarbonyl)-L-prolyl]-4-thiazolidine carbaldehyde dimethyl acetal (4R)-3-[1-((R)-1,2,3,4-tetrahydronaphthalen-2-ylacetyl)-L-prolyl]-4-thiazolidine carbaldehyde dimethyl acetal (4R)-3-[1-[3-((R)-1,2,3,4-tetrahydronaphthalen-2-yl)propanoyl]-L-prolyl]-4-thiazolidine carbaldehyde dimethyl acetal (2S)-1-[3-((R)-1,2,3,4-tetrahydronaphthalen-2-ylcarbonyl)-L-thioprolyl]-2-pyrrolidine carbaldehyde dimethyl acetal (2S)-1-[3-((R)-1,2,3,4-tetrahydronaphthalen-2-ylacetyl)-L-thioprolyl]-2-pyrrolidine carbaldehyde dimethyl acetal (2S)-1-[3-[3-((R)-1,2,3,4-tetrahydronaphthalen-2-yl)propanoyl]-L-thioprolyl]-2-pyrrolidine carbaldehyde dimethyl acetal (4R)-3-[3-((R)-1,2,3,4-tetrahydronaphthalen-2-ylcarbonyl)-L-thioprolyl]-4-thiazolidine carbaldehyde dimethyl acetal (4R)-3-[3-((R)-1,2,3,4-tetrahydronaphthalen-2-ylacetyl)-L-thioprolyl]-4-thiazolidine carbaldehyde dimethyl acetal (4R)-3-[3-[3-((R)-1,2,3,4-tetrahydronaphthalen-2-yl)propanoyl]-L-thioprolyl]-4-thiazolidine carbaldehyde dimethyl acetal (2S)-1-[1-((S)-1,2,3,4-tetrahydronaphthalen-2-ylcarbonyl)-L-prolyl]-2-pyrrolidine carbaldehyde diethyl acetal (2S)-1-[1-((S)-1,2,3,4-tetrahydronaphthalen-2-ylacetyl)-L-prolyl]-2-pyrrolidine carbaldehyde diethyl acetal (2S)-1-[1-[3-((S)-1,2,3,4-tetrahydronaphthalen-2-yl)propanoyl]-L-prolyl]-2-pyrrolidine carbaldehyde diethyl acetal (4R)-3-[1-((S)-1,2,3,4-tetrahydronaphthalen-2-ylcarbonyl)-L-prolyl]-4-thiazolidine carbaldehyde diethyl acetal (4R)-3-[1-((S)-1,2,3,4-tetrahydronaphthalen-2-ylacetyl)-L-prolyl]-4-thiazolidine carbaldehyde diethyl acetal (4R)-3-[1-[3-((S)-1,2,3,4-tetrahydronaphthalen-2-yl)propanoyl]-L-prolyl]-4-thiazolidine carbaldehyde diethyl acetal (2S)-1-[3-((S)-1,2,3,4-tetrahydronaphthalen-2-ylcarbonyl)-L-thioprolyl]-2-pyrrolidine carbaldehyde diethyl acetal (2S)-1-[3-((S)-1,2,3,4-tetrahydronaphthalen-2-ylacetyl)-L-thioprolyl]-2-pyrrolidine carbaldehyde diethyl acetal (2S)-1-[3-[3-((S)-1,2,3,4-tetrahydronaphthalen-2-yl)propanoyl]-L-prolyl]-2-pyrrolidine carbaldehyde diethyl acetal (4R)-3-[3-((S)-1,2,3,4-tetrahydronaphthalen-2-yl-carbonyl)-L-thioprolyl]-4-thiazolidine carbaldehyde diethyl acetal (4R)-3-[3-((S)-1,2,3,4-tetrahydronaphthalen-2-ylacetyl)-L-thioprolyl]-4-thiazolidine carbaldehyde diethyl acetal (4R)-3-[3-[3-((S)-1,2,3,4-tetrahydronaphthalen-2-yl)propanoyl]-L-thioprolyl]-4-thiazolidine carbaldehyde diethyl acetal (2S)-1-[1-((R)-1,2,3,4-tetrahydronaphthalen-2-ylcarbonyl)-L-prolyl]-2-pyrrolidine carbaldehyde diethyl acetal (2S)-1-[1-((R)-1,2,3,4-tetrahydronaphthalen-2-ylacetyl)-L-prolyl]-2-pyrrolidine carbaldehyde diethyl acetal (2S)-1-[1-[3-((R)-1,2,3,4-tetrahydronaphthalen-2-ylpropanoyl]-L-prolyl]-2-pyrrolidine carbaldehyde diethyl acetal (4R)-3-[1-((R)-1,2,3,4-tetrahydronaphthalene-2-ylcarbonyl)-L-prolyl]-4-thiazolidine carbaldehyde diethyl acetal (4R)-3-[1-((R)-1,2,3,4-tetrahydronaphthalen-2-ylacetyl)-L-prolyl]-4-thiazolidine carbaldehyde diethyl acetal (4R)-3-[1-[-3-((R)-1,2,3,4-tetrahydronaphthalen-2-yl)propanoyl]-L-prolyl]-4-thiazolidine carbaldehyde diethyl acetal (2S)-1-[3-((R)-1,2,3,4-tetrahydronaphthalen-2-ylcarbonyl)-L-thioprolyl]-2-pyrrolidine carbaldehyde diethyl acetal (2S)-1-[3-((R)-1,2,3,4-tetrahydronaphthalen-2-ylacetyl)-L-thioprolyl]-2-pyrrolidine carbaldehyde diethyl acetal (2S)-1-[3-[3-((R)-1,2,3,4-tetrahydronaphthalen-2-yl)propanoyl]-L-thioprolyl]-2-pyrrolidine carbaldehyde diethyl acetal (4R)-3-[3-((R)-1,2,3,4-tetrahydronaphthalen-2-ylcarbonyl)-L-thioprolyl]-4-thiazolidine carbaldehyde diethyl acetal (4R)-3-[3-((R)-1,2,3,4-tetrahydronaphthalen-2-ylacetyl)-L-thioprolyl]-4-thiazolidine carbaldehyde diethyl acetal (4R)-3-[3-[3-((R)-1,2,3,4-tetrahydronaphthalen-2-yl)propanoyl]-L-thioprolyl]-4-thiazolidine carbaldehyde diethyl acetal (2S)-1-[1-((S)-1,2,3,4-tetrahydronaphthalen-2-ylcarbonyl)-L-prolyl]-2-pyrrolidine carbaldehyde semicarbazone (2S)-1-[1-((S)-1,2,3,4-tetrahydronaphthalen-2-ylacetyl)-L-prolyl]-2-pyrrolidine carbaldehyde semicarbazone (2S)-1-[1-[3-((S)-1,2,3,4-tetrahydronaphthalen-2-yl)propanoyl]-L-prolyl]-2-pyrrolidine carbaldehyde semicarbazone (4R)-3-[1-((S)-1,2,3,4-tetrahydronaphthalen 2-ylcarbonyl)-L-prolyl]-4-thiazolidine carbaldehyde semicarbazone (4R)-3-[1-((S)-1,2,3,4-tetrahydronaphthalen-2-ylacetyl)-L-prolyl]-4-thiazolidine carbaldehyde semicarbazone (4R)-3-[1-[3-((S)-1,2,3,4-tetrahydronaphthalen -2-yl)propanoyl]-L-prolyl]-4-thiazolidine carbaldehyde semicarbazone (2S)-1-[3-((S)-1,2,3,4-tetrahydronaphthalen-2-ylcarbonyl)-L-thioprolyl]-2-pyrrolidine carbaldehyde semicarbazone (2S)-1-[3-((S)-1,2,3,4-tetrahydronaphthalen-2-ylacetyl)-L-thioprolyl]-2-pyrrolidine carbaldehyde semicarbazone (2S)-1-[3-[3-((S)-1,2,3,4-tetrahydronaphthalen-2-yl)propanoyl]-L-thioprolyl]-2-pyrrolidine carbaldehyde semicarbazone (4R)-3-[3-((S)-1,2,3,4-tetrahydronaphthalen-2-ylcarbonyl)-L-thioprolyl]-4-thiazolidine carbaldehyde semicarbazone (4R)-3-[3-((S)-1,2,3,4-tetrahydronaphthalen-2-ylacetyl)-L-thioprolyl]-4-thiazolidine carbaldehyde semicarbazone (4R)-3-[3-[3-((S)-1,2,3,4-tetrahydronaphthalen-2-yl)propanoyl]-L-thioprolyl]-4-thiazolidine carbaldehyde semicarbazone (2S)-1-[1-(benzofuran-2-ylcarbonyl)-L-prolyl]-2-pyrrolidine aldoxime (2S)-1-[1-(benzofuran-2-ylacetyl)-L-prolyl]-2-pyrrolidine aldoxime (2S)-1-[1-[3-(benzofuran-2-yl)propanoyl]-L-prolyl]-2-pyrrolidine aldoxime (4R)-3-[1-(benzofuran-2-ylcarbonyl)-L-prolyl]-4-thiazolidine aldoxime (4R)-3-[1-(benzofuran-2-ylacetyl)-L-prolyl]-4-thiazolidine aldoxime (4R)-3-[1-[3-(benzofuran-2-yl)propanoyl]-L-prolyl]-4-thiazolidine aldoxime (2S)-1-[3-(benzofuran-2-ylcarbonyl)-L-thioprolyl]-2-pyrrolidine aldoxime (2S)-1-[3-(benzofuran-2-ylacetyl)-L-thioprolyl]-2-pyrrolidine aldoxime (2S)-1-[3-[3-(benzofuran-2-yl)propanoyl]-L-thioprolyl]-2-pyrrolidine aldoxime (4R)-3-[3-(benzofuran-2-ylcarbonyl)-L-thioprolyl]-4-thiazolidine aldoxime (4R)-3-[3-(benzofuran-2-ylacetyl)-L-thioprolyl]-4-thiazolidine aldoxime (4R)-3-[3-[3-(benzofuran-2-yl)propanoyl]-L-thioprolyl]-4-thiazolidine aldoxime (2S)-1-[1-(benzofuran-2-ylcarbonyl)-L-prolyl]-2-cyanopyrrolidine (2S)-1-[1-(benzofuran-2-ylacetyl)-L-prolyl]-2-cyanopyrrolidine (2S)-1-[1-[3-(benzofuran-2-yl)propanoyl]-L-thioprolyl]-2-cyanopyrrolidine (4R)-3-[1-(benzofuran-2-ylcarbonyl)-L-prolyl]-4-cyanothiazolidine (4R)-3-[1-(benzofuran-2-ylacetyl)-L-prolyl]-4-cyanothiazolidine (4R)-3-[1-[3-(benzofuran-2-yl)propanoyl]-L-prolyl]-4-cyanothiazolidine (2S)-1-[3-(benzofuran-2-ylcarbonyl)-L-thioprolyl]-2-cyanopyrrolidine (2S)-1-[3-(benzofuran-2-ylacetyl)-L-thioprolyl]-2-cyanopyrrolidine (2S)-1-[3-[3-(benzofuran-2-yl)propanoyl]-L-thioprolyl]-2-cyanopyrrolidine (4R)-3-[3-(benzofuran-2-ylcarbonyl)-L-thioprolyl]-4-cyanothiazolidine (4R)-3-[3-(benzofuran-2-ylacetyl)-L-thioprolyl]-4-cyanothiazolidine (4R)-3-[3-[3-(benzofuran-2-yl)propanoyl]-L-thioprolyl]-4-cyanothiazolidine (2S)-1-[1-(benzofuran-2-ylcarbonyl)-L-prolyl]-2-pyrrolidine carbaldehyde dimethyl acetal (2S)-1-[1-(benzofuran-2-ylacetyl)-L-prolyl]-2-pyrrolidine carbaldehyde dimethyl acetal (2S)-1-[1-[3-(benzofuran-2-yl)propanoyl]-L-prolyl]-2-pyrrolidine carbaldehyde dimethyl acetal (4R)-3-[1-(benzofuran-2-ylcarbonyl)-L-prolyl]-4-thiazolidine carbaldehyde dimethyl acetal (4R)-3-[1-(benzofuran-2-ylacetyl)-L-prolyl]-4-thiazolidine carbaldehyde dimethyl acetal (4R)-3-[1-[3-(benzofuran-2-yl)propanoyl]-L-prolyl]-4-thiazolidine carbaldehyde dimethyl acetal (2S)-1-[3-(benzofuran-2-ylcarbonyl)-L-thioprolyl]-2-pyrrolidine carbaldehyde dimethyl acetal (2S)-1-[3-(benzofuran-2-ylacetyl)-L-thioprolyl]-2-pyrrolidine carbaldehyde dimethyl acetal
(2S)-1-[3-[3-(benzofuran-2-yl)propanoyl]-L-thioprolyl]-2-pyrrolidine carbaldehyde dimethyl acetal
(4R)-3-[3-(benzofuran-2-ylcarbonyl)-L-thioprolyl]-4-thiazolidine carbaldehyde dimethyl acetal
(4R)-3-[3-(benzofuran-2-ylacetyl)-L-thioprolyl]-4-thiazolidine carbaldehyde dimethyl acetal
(4R)-3-[3-[3-(benzofuran-2-yl)propanoyl]-L-thioprolyl]-4-thiazolidine carbaldehyde dimethyl acetal
(2S)-1-[1-(benzofuran-2-ylcarbonyl)-L-prolyl]-2-pyrrolidine carbaldehyde diethyl acetal
(2S)-1-[1-(benzofuran-2-ylacetyl)-L-prolyl]-2-pyrrolidine carbaldehyde diethyl acetal
(2S)-1-[1-[3-(benzofuran-2-yl)propanoyl]-L-prolyl]-2-pyrrolidine carbaldehyde diethyl acetal
(4R)-3-[1-(benzofuran-2-ylcarbonyl)-L-prolyl]-4-thiazolidine carbaldehyde diethyl acetal
(4R)-3-[1-(benzofuran-2-ylacetyl)-L-prolyl]-4-thiazolidine carbaldehyde diethyl acetal
(4R)-3-[1-[3-(benzofuran-2-yl)propanoyl]-L-prolyl]-4-thiazolidine carbaldehyde diethyl acetal
(2S)-1-[3-(benzofuran-2-ylcarbonyl)-L-thioprolyl]-2-thiazolidine carbaldehyde diethyl acetal
(2S)-1-[3-(benzofuran-2-ylacetyl)-L-thioprolyl]-2-thiazolidine carbaldehyde diethyl acetal
(2S)-1-[3-[3-(benzofuran-2-yl)propanoyl]-L-thioprolyl]-2-thiazolidine carbaldehyde diethyl acetal
(4R)-3-[3-(benzofuran-2-ylcarbonyl)-L-thioprolyl]-4-thiazolidine carbaldehyde diethyl acetal
(4R)-3-[3-(benzofuran-2-ylacetyl)-L-thioprolyl]-4-thiazolidine carbaldehyde diethyl acetal
(4R)-3-[3-[3-(benzofuran-2-yl)propanoyl]-L-thioprolyl]-4-thiazolidine carbaldehyde diethyl acetal
(2S)-1-[1-(benzofuran-2-ylcarbonyl)-L-prolyl]-2-pyrrolidine carbaldehyde semicarbazone
(2S)-1-[1-(benzofuran-2-ylacetyl)-L-prolyl]-2-pyrrolidine carbaldehyde semicarbazone
(2S)-1-[1-[3-(benzofuran-2-yl)propanoyl]-L-prolyl]-2-pyrrolidine carbaldehyde semicarbazone
(4R)-3-[1-(benzofuran-2-ylcarbonyl)-L-prolyl]-4-thiazolidine carbaldehyde semicarbazone
(4R)-3-[1-(benzofuran-2-ylacetyl)-L-prolyl]-4-thiazolidine carbaldehyde semicarbazone
(4R)-3-[1-[3-(benzofuran-2-yl)propanoyl]-L-prolyl]-4-thiazolidine carbaldehyde semicarbazone
(2S)-1-[3-(benzofuran-2-ylcarbonyl)-L-thioprolyl]-2-pyrrolidine carbaldehyde semicarbazone
(2S)-1-[3-(benzofuran-2-ylacetyl)-L-thioprolyl]-2-pyrrolidine carbaldehyde semicarbazone
(2S)-1-[3-[3-(benzofuran-2-yl)propanoyl]-L-thioprolyl]-2-pyrrolidine carbaldehyde semicarbazone
(4R)-3-[3-(benzofuran-2-ylcarbonyl)-L-thioprolyl]-4-thiazolidine carbaldehyde semicarbazone
(4R)-3-[3-(benzofuran-2-ylacetyl)-L-thioprolyl]-4-thiazolidine carbaldehyde semicarbazone
(4R)-3-[3-[3-(benzofuran-2-yl)propanoyl]-L-thioprolyl]-4-thiazolidine carbaldehyde semicarbazone
(2S)-1-[1-(inden-2-ylcarbonyl)-L-prolyl]-2-pyrrolidine aldoxime
(2S)-1-[1-(inden-2-ylacetyl)-L-prolyl]-2-pyrrolidine aldoxime
(2S)-1-[1-[3-(inden-2-yl)propanoyl]-L-prolyl]-2-pyrrolidine aldoxime
(4R)-3-[1-(inden-2-ylcarbonyl)-L-prolyl]-4-thiazolidine aldoxime
(4R)-3-[1-(inden-2-ylacetyl)-L-prolyl]-4-thiazolidine aldoxime
(4R)-3-[1-[3-(inden-2-yl)propanoyl]-L-prolyl]-4-thiazolidine aldoxime
(2S)-1-[3-(inden-2-ylcarbonyl)-L-thioprolyl]-2-pyrrolidine aldoxime
(2S)-1-[3-(inden-2-ylacetyl)-L-thioprolyl]-2-pyrrolidine aldoxime
(2S)-1-[3-[3-(inden-2-yl)propanoyl]-L-thioprolyl]-2-pyrrolidine aldoxime
(4R)-3-[3-(inden-2-ylcarbonyl)-L-thioprolyl]-4-thiazolidine aldoxime
(4R)-3-[3-(inden-2-ylacetyl)-L-thioprolyl]-4-thiazolidine aldoxime
(4R)-3-[3-[3-(inden-2-yl)propanoyl]-L-thioprolyl]-4-thiazolidine aldoxime
(2S)-1-[1-(inden-2-ylcarbonyl)-L-prolyl]-2-cyanopyrrolidine
(2S)-1-[1-(inden-2-ylacetyl)-L-prolyl]-2-cyanopyrrolidine
(2S)-1-[1-[3-(inden-2-yl)propanoyl]-L-prolyl]-2-cyanopyrrolidine
(4R)-3-[1-(inden-2-ylcarbonyl)-L-prolyl]-4-cyanothiazolidine
(4R)-3-[1-(inden-2-ylacetyl)-L-prolyl]-4-cyanothiazolidine
(4R)-3-[1-[3-(inden-2-yl)propanoyl]-L-prolyl]-4-cyanothiazolidine
(2S)-1-[3-(inden-2-ylcarbonyl)-L-thioprolyl]-2-cyanopyrrolidine
(2S)-1-[3-(inden-2-ylacetyl)-L-thioprolyl]-2-cyanopyrrolidine
(2S)-1-[3-[3-(inden-2-yl)propanoyl]-L-thioprolyl]-2-cyanopyrrolidine
(4R)-3-[3-(inden-2-ylcarbonyl)-L-thioprolyl]-4-cyanothiazolidine
(4R)-3-[3-(inden-2-ylacetyl)-L-thioprolyl]-4-cyanothiazolidine
(4R)-3-[3-[3-(inden-2-yl)propanoyl]-L-thioprolyl]-4-cyanothiazolidine
(2S)-1-[1-(inden-2-ylcarbonyl)-L-prolyl]-2-pyrrolidine carbaldehyde dimethyl acetal
(2S)-1-[1-(inden-2-ylacetyl)-L-prolyl]-2-pyrrolidine carbaldehyde dimethyl acetal
(2S)-1-[1-[3-(inden-2-yl)propanoyl]-L-prolyl]-2-pyrrolidine carbaldehyde dimethyl acetal
(4R)-3-[1-(inden-2-ylcarbonyl)-L-prolyl]-4-thiazolidine carbaldehyde dimethyl acetal
(4R)-3-[1-(inden-2-ylacetyl)-L-prolyl]-4-thiazolidine carbaldehyde dimethyl acetal
(4R)-3-[1-[3-(inden-2-yl)propanoyl]-L-prolyl]-4-thiazolidine carbaldehyde dimethyl acetal
(2S)-1-[3-(inden-2-ylcarbonyl)-L-thioprolyl]-2-pyrrolidine carbaldehyde dimethyl acetal
(2S)-1-[3-(inden-2-ylacetyl)-L-thioprolyl]-2-pyrrolidine carbaldehyde dimethyl acetal
(2S)-1-[3-[3-(inden-2-yl)propanoyl]-L-thioprolyl]-2-pyrrolidine carbaldehyde dimethyl acetal
(4R)-3-[3-(inden-2-ylcarbonyl)-L-thioprolyl]-4-thiazolidine carbaldehyde dimethyl acetal
(4R)-3-[3-(inden-2-ylacetyl)-L-thioprolyl]-4-thiazolidine carbaldehyde dimethyl acetal
(4R)-3-[3-[3-(inden-2-yl)propanoyl]-L-thioprolyl]-4-thiazolidine carbaldehyde dimethyl acetal
(2S)-1-[1-(inden-2-ylcarbonyl)-L-prolyl]-2-pyrrolidine carbaldehyde diethyl acetal
(2S)-1-[1-(inden-2-ylacetyl)-L-prolyl]-2-pyrrolidine carbaldehyde diethyl acetal
(2S)-1-[1-[3-(inden-2-yl)propanoyl]-L-thioprolyl]-2-pyrrolidine carbaldehyde diethyl acetal (4R)-3-[1-(inden-2-ylcarbonyl)-L-prolyl]-4-thiazolidine carbaldehyde diethyl acetal
(4R)-3-[1-(inden-2-ylacetyl)-L-prolyl]-4-thiazolidine carbaldehyde diethyl acetal
(4R)-3-[1-[3-(inden-2-yl)propanoyl]-L-prolyl]-4-thiazolidine carbaldehyde diethyl acetal
(2S)-1-[3-(inden-2-ylcarbonyl)-L-thioprolyl]-2-pyrrolidine carbaldehyde diethyl acetal
(2S)-1-[3-(inden-2-ylacetyl)-L-thioprolyl]-2-pyrrolidine carbaldehyde diethyl acetal
(2S)-1-[3-[3-(inden-2-yl)propanoyl]-L-thioprolyl]-2-pyrrolidine carbaldehyde diethyl acetal
(4R)-3-[3-(inden-2-ylcarbonyl)-L-thioprolyl]-4-thiazolidine carbaldehyde diethyl acetal
(4R)-3-[3-(inden-2-ylacetyl)-L-thioprolyl]-4-thiazolidine carbaldehyde diethyl acetal
(4R)-3-[3-[3-(inden-2-yl)propanoyl]-L-thioprolyl]-4-thiazolidine carbaldehyde diethyl acetal
(2S)-1-[1-(inden-2-ylcarbonyl)-L-prolyl]-2-pyrrolidine carbaldehyde semicarbazone
(2S)-1-[1-(inden-2-ylacetyl)-L-prolyl]-2-pyrrolidine carbaldehyde semicarbazone
(2S)-1-[1-[3-(inden-2-yl)propanoyl]-L-prolyl]-2-pyrrolidine carbaldehyde semicarbazone
(4R)-3-[1-(inden-2-ylcarbonyl)-L-prolyl]-4-thiazolidine carbaldehyde semicarbazone
(4R)-3-[1-(inden-2-ylacetyl)-L-prolyl]-4-thiazolidine carbaldehyde semicarbazone
(4R)-3-[1-[3-(inden-2-yl)propanoyl]-L-prolyl]-4-thiazolidine carbaldehyde semicarbazone
(2S)-1-[3-(inden-2-ylcarbonyl)-L-thioprolyl]-2-pyrrolidine carbaldehyde semicarbazone
(2S)-1-[3-(inden-2-ylacetyl)-L-thioprolyl]-2-pyrrolidine carbaldehyde semicarbazone
(2S)-1-[3-[3-(inden-2-yl)propanoyl]-L-thioprolyl]-2-pyrrolidine carbaldehyde semicarbazone
(4R)-3-[3-(inden-2-ylcarbonyl)-L-thioprolyl]-4-thiazolidine carbaldehyde semicarbazone
(4R)-3-[3-(inden-2-ylacetyl)-L-thioprolyl]-4-thiazolidine carbaldehyde semicarbazone
(4R)-3-[3-[3-(inden-2-yl)propanoyl]-L-thioprolyl]-4-thiazolidine carbaldehyde semicarbazone These compounds (I) of the present invention can be produced, for example, by any of the methods (a), (b) and (c) described below.

Method (a)

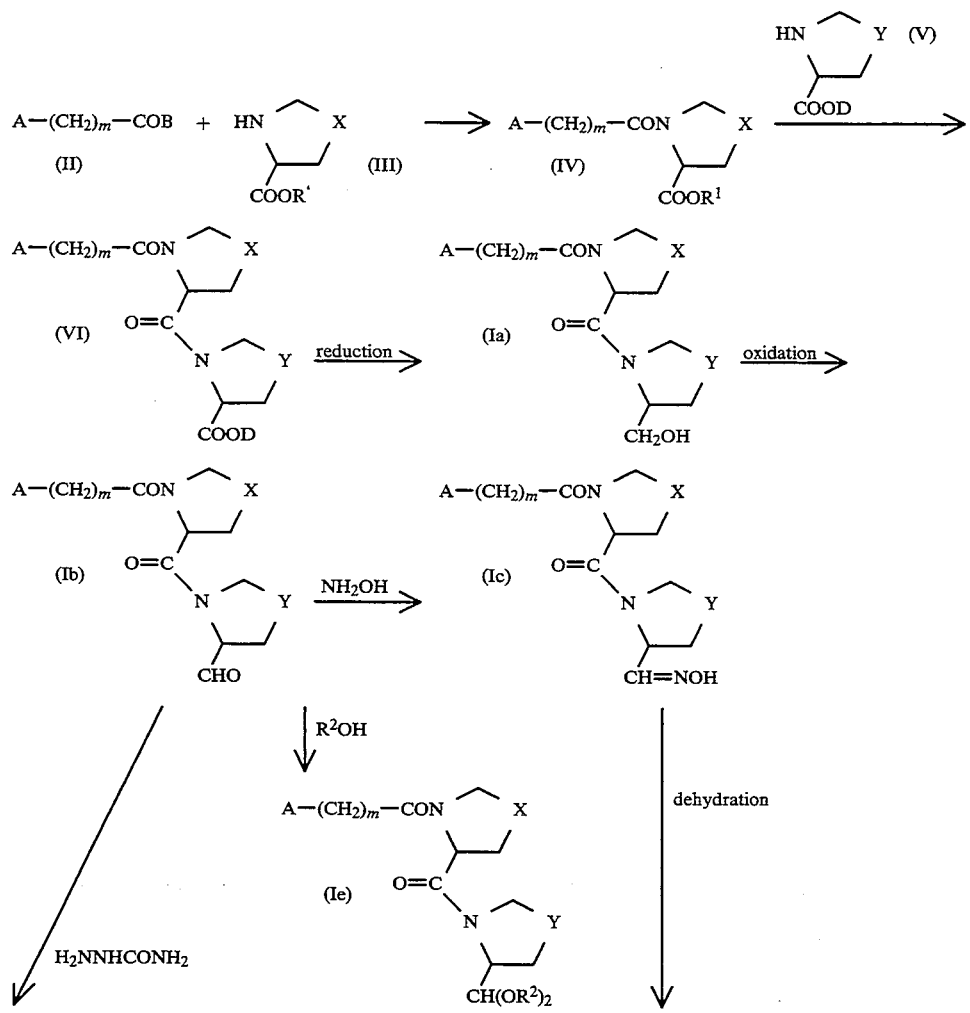

-continued
Method (a)

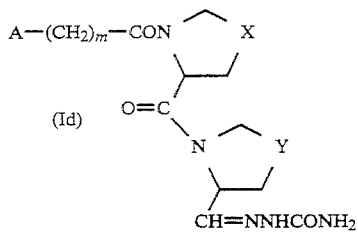
(Id)

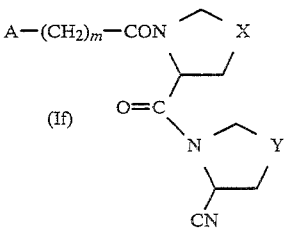
(If)

(wherein B represents halogen atom, a lower alkoxy group or hydroxyl group; R1 represents hydrogen atom or a lower alkyl group; R2 and D represent a lower alkyl group; A, m, X and Y represent the same meaning as described above).

That is, a cyclic amino acid compound (III) reacts with an arylalkane derivative (II) to produce an N-substituted cyclic amino acid derivative (IV), with which a cyclic amino acid compound (V) reacts to obtain a compound (VI). The compound (Ia) of the present invention wherein Z is hydroxymethyl group can be obtained by subsequently reducing the compound (VI). By further oxidation of the compound (Ia), the compound (Ib) of the present invention wherein Z is formyl group can be obtained. When hydroxylamine reacts with the compound (Ib), the compound (Ic) of the present invention wherein Z is hydroxyiminomethyl group can be obtained; When semicarbazide reacts with the compound (Ib), the compound (Id) of the present invention wherein Z is semicarbazonomethyl group can be obtained; and when alcohol reacts with the compound (Ib), the compound (Ie) of the present invention wherein Z is alkoxymethyl group can be obtained. When the compound (Ic) is dehydrated, the compound (If) of the present invention wherein Z is nitrile group can be obtained.

The reaction of the arylalkanoic acid derivative (II) with the cyclic amino acid compound (III) follows general reaction for generating acid amide. Of the arylalkanoic acid derivative (II), the one wherein B is halogen atom or a lower alkoxy group is subjected to condensation reaction in the presence or absence of a base. When B is hydroxyl group, it is preferred to use carbodiimides as the condensation agent. Examples of the base to be used in the reaction include an alkali metal hydroxide or carbonate, trialkyl amine, aromatic amine and the like; preferable examples thereof are sodium hydroxide, potassium hydroxide and the like; preferable examples of carbodiimides include 1-ethyl-3-(3-dimethylaminopropyl)carbodiimide (WSC) or the hydrochloride salt thereof (WSC.HCl), N, N'-dicylohexylcarbodiimide (DCC) and the like. The reaction temperature is −20° to 200° C., and any solvent never involved in such reaction may be satisfactory. Of the N-substituted cyclic amino acid derivative (IV), the one wherein R1 is a lower alkyl group can be hydrolyzed into carboxylic acid wherein R1 is hydrogen atom.

The reaction of the N-substituted amino acid derivative (IV) with the cyclic amino acid compound (V) is carried out following general condensation reaction. Such condensing agent if used may be any one generally employed, and preferably, the agent are carbodiimides such as WSC, WSC.HCl, DCC and the like. As the solvent, any solvent never involved in the reaction may be satisfactory, preferably including methylene chloride, chloroform, tetrahydrofuran, dioxane and the like, and the reaction temperature is −20° to 80° C., preferably 0° to 40° C. Also, other condensation methods generally used, for example, acid chloride method, method with anhydrous mixed acids or the like, may be satisfactory (Fundamentals and Experimentals of Peptide Synthesis, Izumiya, et al., Maruzen (1985)).

The reduction of the compound (VI) may be done by general method by using a reducing agent. As the reducing agent, preference is given to metal borohydrides such as sodium borohydride, lithium borohydride, zinc borohydride, potassium borohydride and the like. As the solvent, preference is given to alcohols such as methanol, ethanol, propanol, isopropanol, butanol, t-butanol and the like and to ethers such as tetrahydrofuran, dioxane and the like.

The oxidation of the compound (Ia) is done in the presence or absence of an inactive organic solvent such as methylene chloride, chloroform, benzene and the like in a range of −80° to 100° C., by using as an oxidizing agent dimethyl sulfoxide, chromium trioxide-pyridine complex, t-butyl chromate, silver oxide, manganese dioxide and the like. If dimethyl sulfoxide is used as the oxidizing agent, it is preferred to effect the oxidation in the co-presence of an activating agent such as sulfur trioxide-pyridine complex, oxalyl chloride, DCC and the like.

The reaction of the compound (Ib) with hydroxyl amine or the salt thereof and the reaction of the compound (Ib) with semicarbazide or the salt thereof are done in the presence or absence of a base according to the general method.

The reaction of the compound (Ib) with alcohol is done in the presence or absence of an acid catalyst according to the general method.

The dehydration of the compound (Ic) is done by general dehydration reaction. For example, such dehydration is done in the absence of solvents or an inactive solvent such as benzene, chloroform, ether and the like at room temperature or the reflux temperature, by using formic acid, acetic acid, acetic anhydride, phosphorous pentaoxide, thionyl chloride and the like.

The compound (If) can be obtained also from the compound (Ib) without isolation of the compound (Ic). For example, the compound (Ib) and hydroxyl amine hydrochloride react together in an inactive solvent such as dimethyl formamide and the like in the presence of a base such as pyridine and triethylamine, at room temperature to the reflux temperature, followed by addition of selenium dioxide for dehydration, to prepare the compound (If). The compound (If) can be obtained by the dehydration of the corresponding amide, as well.

Method (b)

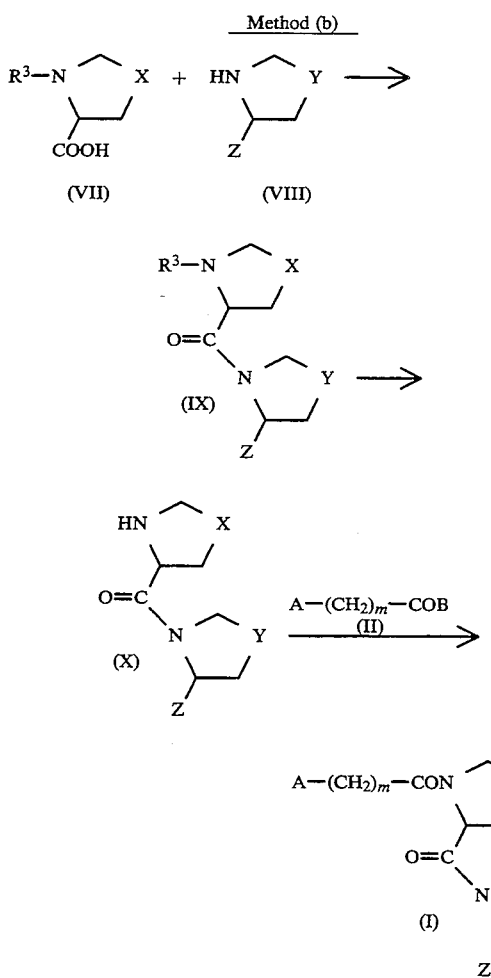

(wherein R3 represents the protective group of amino group; A, m, B, X, Y and Z are the same meaning as described above.)

That is, the cyclic amine (VIII) reacts with the cyclic amino acid compound (VII), and the protective group of the amino group of the resulting compound (IX) is eliminated to produce the compound (X), followed by the reaction with the arylalkanoic acid derivative (II) to obtain the compound (I) of the present invention.

The reaction of the cyclic amino acid compound (VII) with the cyclic amine (VIII) and the reaction of the compound (X) with the arylalkanoic acid derivative (II) are done in the same manner as described in the Method (a). The elimination of the amino group of the compound (IX) can be effected by general method.

By subjecting the resulting compound (Ia) of the present invention to the reaction as described in the Method (a), the compounds (Ib), (Ic), (Id), (Ie) and (If) may be obtained.

Method (c)

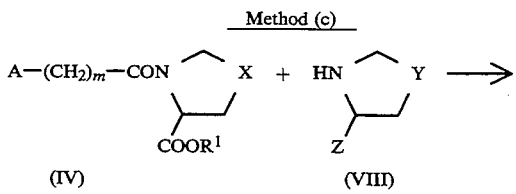

-continued
Method (c)

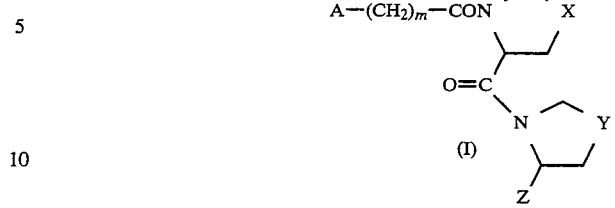

(wherein A, m, X, Y, Z and R1 represent the same meaning as described above.)

That is, the compound (I) of the present invention can be obtained by condensing the N-substituted cyclic amino acid derivative (IV) with the cyclic amine (VIII). This condensation reaction may be done as in the Method described above.

By subjecting the resulting compound (Ia) of the present invention to the reaction as shown in the Method (a), the compounds (Ib), (Ic), (Id), (Ie) and (If) may be obtained.

If carbodiimides are herein used as a condensing agent in the condensation reaction, a part of the resulting product may be subjected to racemization in some cases. In such cases, it is preferred to employ a method by mixed acid anhydride. For example, the reaction is effected in an inactive solvent such as methylene chloride, chloroform, ether and the like in the presence of a base such as triethylamine, pyridine, N-methylmorpholine and the like in a range of 0° to 50° C., by using acid halides such as pivaloyl chloride, tosyl chloride and the like or acid derivatives such as ethyl chloroformate, isobutyl chloroformate and the like.

The compound (I) of the present invention prepared by the manner discussed above exhibits prolyl endopeptidase inhibitory activity, anti-hypoxic activity, and anti-amnesic activity at the same time, and is a highly safe compound. It is therefore useful as a drug for improving mneme, cerebral circulation and cerebral metabolism.

Drugs for improving mneme, cerebral circulation and cerebral metabolism with the effective compound being the compound (I) of the present invention may be prepared into formulations for oral or parenteral administration, by compounding pharmaceutically acceptable additives. In case of formulations for oral administration, the compound can be formulated into tablets, powders, granules and capsules, by appropriate combinations thereof with excipients such as lactose, mannitol, corn starch, crystalline cellulose and the like; binders such as cellulose derivatives, gum arabic, gelatin and the like; disintegrating agents such as carboxymethyl cellulose calcium and the like; and lubricants such as talc, magnesium stearate and the like. These solid formulations can be prepared into enteric coated formulations, by using a coating base such as hydroxypropylmethyl cellulose terephthalate, hydroxypropylmethyl cellulose acetate succinate, cellulose acetate phthalate, methacrylate copolymer and the like. In case of formulations for parenteral administration, the compound can be formulated into injectable solutions by combination with, for example, water, ethanol, glycerin, routine surfactants and the like, and can be formulated into suppositories by using a base for suppositories.

The dose of the compound (I) of the present invention varies depending on the age, body weight, symptom, therapeutic effect, dosage, and period for administration, but generally the oral dose is in a range of 0.1 to 2,000 mg/day, preferably 1 to 200 mg/day, which is preferably divided in a range of 1 to 3 for administration.

EXAMPLES

The present invention will now be described in details with reference to examples, but the invention is not limited to them.

EXAMPLE 1

1-[3-(Indan-2-ylacetyl)-L-thioprolyl]-L-prolinol

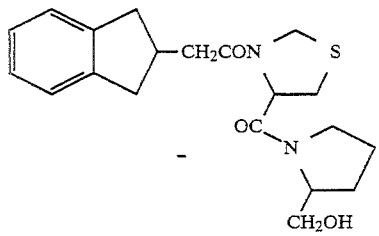

3-(Indan-2-ylacetyl)-L-thioproline (4.40 g) and L-prolinol (1.53 g) were dissolved in 150 ml of methylene chloride, followed by addition of 2.90 g of WSC-HCl under agitation while cooling in ice and subsequent agitation for another 30 minutes at room temperature. The reaction solution was washed sequentially in 5 HCl, saturated aqueous solution of sodium bicarbonate, saturated aqueous sodium chloride solution, followed by drying over anhydrous magnesium sulfate. After distilling off the solvent under reduced pressure, the residue was purified by column chromatography to obtain 2.40 g of 1-[3-(indan-2-yl-acetyl)-L-thioprolyl]-L-prolinol. Yield; 42%.

IR(neat)cm$^{-1}$: 3400, 3000~2800, 1640, 1420, 740 NMR (CDCl$_3$) δ ppm: 1.60~2.10(4H, m), 2.50~2.70 (4H, m), 2.90~3.40 (5H, m), 3.46~4.20 (5H, m), 4.35~4.85(3H, m), 5.00~5.55(1H, m), 7.10~7.25(4H, m)

EXAMPLE 2

1-[3-(Indan-2-ylacetyl)-L-thioprolyl]-L-prolinal

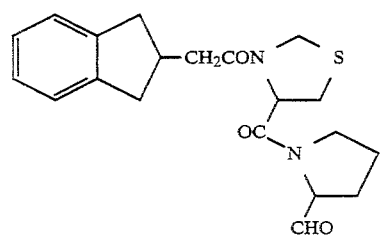

1-[3-(Indan-2-ylacetyl)-L-thioprolyl]-L-prolinol (590 mg) and trimethylamine (1.32 ml) were dissolved in 1.50 ml of dimethyl sulfoxide, followed by addition of 1.55 g of sulfur trioxide-pyridine complex dissolved in 2.25 ml of dimethyl sulfoxide at room temperature under agitation, which was then agitated for 15 minutes. The reaction solution was placed in ice-cold water, followed by extraction with chloroform. The organic phase was washed sequentially in 5% HCl, saturated aqueous sodium bicarbonate solution, saturated aqueous sodium chloride solution, followed by drying over anhydrous magnesium sulfate. After distilling off the solvent under reduced pressure, the residue was purified by column chromatography, to obtain 107 mg of 1-[3-(indan-2-yl acetyl)-L-thioprolyl]-L-prolinal. Yield; 18%.

IR(neat)cm$^{-1}$: 3400, 3100~2800, 1730, 1640, 1420, 750 NMR (CDCl$_3$) δ ppm: 1.80~2.20 (4H, m), 2.50~3.40 (9H, m), 3.55~4.10 (2H, m), 4.25~4.65 (1H, m), 4.60 (2H, m), 5.00~5.20 (1H, m), 7.10~7.20 (4H, m), 9.40~9.60(1H, m)

EXAMPLES 3 TO 12

Following the same method as in Examples 1 and 2, the compounds shown in table 1 were obtained.

EXAMPLE 3

3-[1-(Indan-2,ylacetyl)-L-prolyl]-L-thioprolinol

EXAMPLE 4

1-[3-((S)-1,2,3,4-tetrahydronaphthalen-2-ylacetyl)-L-thioprolyl]-L-prolinol

EXAMPLE 5

3-[3-((S)-1,2,3,4-tetrahydronaphthalen 2-ylacetyl)-L-thioprolyl]-L-thioprolinol

EXAMPLE 6

1-[1-(benzofuran-2-ylcarbonyl)-L-prolyl]-L-prolinol

EXAMPLE 7

3-[1-(benzofuran-2-ylcarbonyl)-L-prolyl]-L-thioprolinol

EXAMPLE 8

3-[1-(indan-2-ylacetyl)-L-prolyl]-L-thioprolinal

EXAMPLE 9

1-[3-((S)-1,2,3,4-tetrahydronaphthalen-2-ylacetyl)-L-thioprolyl]-L-prolinal

EXAMPLE 10

3-[3-((S)-1,2,3,4-tetrahydronaphthalen-2-ylacetyl)-L-thioprolyl]-L-thioprolinal

EXAMPLE 11

1-[1-(benzofuran-2-ylcarbonyl)-L-prolyl]-L-prolinal

EXAMPLE 12

3-[1-(benzofuran-2-ylcarbonyl)-L-prolyl]-L-thioprolinal

TABLE 1

Arylalkanoylamine Derivatives [Formula(I)]

| Ex. No. | A | m | X | Y | Z | Yield (%) | IR (cm⁻¹) | NMR (δppm) |
|---|---|---|---|---|---|---|---|---|
| 3 | 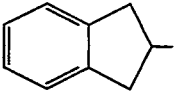 | 1 | CH₂ | S | CH₂OH | 65 | (KBr): 3360, 2900, 1630, 1420, 750 | (CDCl₃): 1.80–2.25(5H, m), 2.38–2.71(4H, m), 2.81–2.97(2H, m), 3.11–3.28(3H, m), 3.46–3.72(3H, m), 3.98–4.06(1H, m), 4.39(1H, d, J=9Hz), 4.48–4.55(1H, m), 5.00(1H, d, J=9Hz), 5.08–5.13(1H, m), 7.10–7.18(4H, m) |
| 4 | 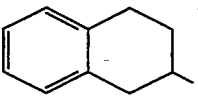 | 1 | S | CH₂ | CH₂OH | 66 | (KBr): 3400, 2910, 1625, 1410, 740 | (CDCl₃): 1.43–2.20(6H, m), 2.30–2.61(4H, m), 2.82–4.40(10H, m), 4.43–4.90(3H, m), 4.92–5.54(1H, m), 7.02–7.25(4H, m) |
| 5 | 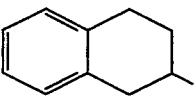 | 1 | S | S | CH₂OH | 77 | (KBr): 3400, 2910, 1630, 1410, 740 | (CDCl₃): 1.43–1.60(1H, m), 1.95–2.10(1H, m), 2.32–2.60(4H, m), 2.79–3.42(7H, m), 3.64–4.12(2H, m), 4.38–5.08(5H, m), 5.10–5.48(1H, m), 7.03–7.08(4H, m) |
| 6 | 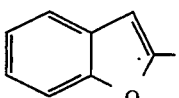 | 0 | CH₂ | CH₂ | CH₂OH | 63 | (KBr): 3420, 2950, 2860, 1620, 1420, 740 | (CDCl₃): 1.72–2.57(8H, m), 3.48–4.47(7H, m), 4.80–5.40(2H, m), 7.23–7.75(5H, m) |
| 7 | 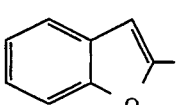 | 0 | CH₂ | S | CH₂OH | 73 | (KBr): 3400, 2850, 1620, 1560, 1420, 740 | (CDCl₃): 1.92–2.43(4H, m), 2.85–3.00(1H, m), 3.17–3.38(1H, m), 3.65–3.82(2H, m), 4.00–4.33(2H, m), 4.40(1H, d, J=10Hz), 4.49–5.33 (4H, m), 7.27–7.72(5H, m) |
| 8 | 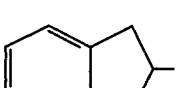 | 1 | CH₂ | S | CHO | 25 | (neat): 3350, 2900–2800, 1725, 1610, 1420, 740 | (CDCl₃): 1.91–2.40(4H, m), 2.40–2.72(4H, m), 2.90–3.40(5H, m), 3.45–3.70(2H, m), 4.52–4.80(2H, m), 5.00–5.21(2H, m), 7.14–7.30(4H, m), 9.52–9.70(1H, m) |
| 9 | 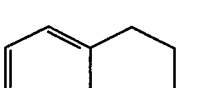 | 1 | S | CH₂ | CHO | 13 | (KBr): 3430, 2920, 1725, 1635, 1410, 745 | (CDCl₃): 1.38–1.57(1H, m), 1.85–2.58(9H, m), 2.75–3.00(3H, m), 3.18–3.42(2H, m), 3.45–4.07(2H, m), 4.57–4.78(3H, m), 5.03–5.22(1H, m), 6.98–7.17(4H, m), 9.40–9.61(1H, m) |
| 10 | 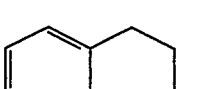 | 1 | S | S | CHO | 16 | (KBr): 3430, 2920, 1730, 1635, 1410, 745 | (CDCl₃): 1.37–1.60(1H, m), 1.86–2.02(1H, m), 2.20–2.57(4H, m), 2.77–3.00(3H, m), 3.05–3.47(4H, m), 4.47–4.80(4H, m), 4.95–5.55(2H, m), 6.93–7.15(4H, m), 9.45–9.60(1H, m) |
| 11 | 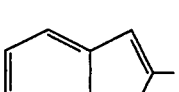 | 0 | CH₂ | CH₂ | CHO | 13 | (KBr): 3450, 2960, 1730, 1645, 1620, 1420, 740 | (CDCl₃): 1.80–2.45(8H, m), 3.45–4.23(4H, m), 4.45–4.95(2H, m), 7.20–7.67(5H, m), 9.50 (1H, s) |
| 12 | 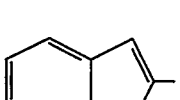 | 0 | CH₂ | S | CHO | 26 | (KBr): 3400, 2950, 1730, 1650, 1620, 1405, 740 | (CDCl₃): 1.86–2.47(4H, m), 3.05–3.63(2H, m), 3.77–4.25(2H, m), 4.45–5.45(4H, m), 7.20–7.72(5H, m), 9.50–9.58(1H, m) |

EXAMPLE 13

1-[3-(Indan-2-ylacetyl)-L-thioprolyl]-L-prolinol

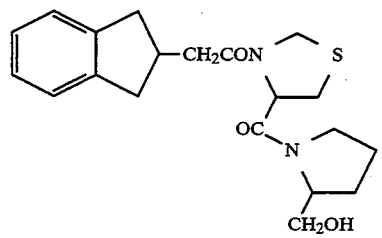

3-(Indan-2-ylacetyl)-L-thioproline (11.7 g) and triethylamine (5.6 ml) were dissolved in 100 ml of methylene chloride, followed by dropwise addition of 4.95 g of pivaloyl chloride under agitation while cooling in ice for 15 minutes. Subsequently, 4.05 g of L-prolinol and 5.6 ml of triethylamine were added dropwise and stirred at room temperature for another one hour. The reaction solution were washed in 1N HCl, saturated aqueous solution of sodium bicarbonate and saturated sodium chloride solution, dried over anhydrous magnesium sulfate, followed by distillation of the solvent under reduced pressure. The resulting residue was purified by column chromatography to obtain 8.80 g of 1-[3-(indan-2-ylacetyl)-L-thioprolyl]-L-prolinol. Yield; 59%.

IR(neat)cm$^{-1}$: 3600~3100, 3000~2800, 1630, 1410, 740 NMR (CDCl$_3$) δ ppm: 1.60~2.12(4H, m), 2.52~2.69 (4H, m), 2.90~3.37 (5H, m), 3.44~4.35 (5H, m), 4.40~4.85 (3H, m), 5.07 & 5.41 (total 1H, each t, J=7 Hz), 7.10~7.20 (4H, m)

EXAMPLE 14

(2S)-1-[3-(Indan-2-ylacetyl)-L-thioprolyl]-2-pyrrolidine aldoxime

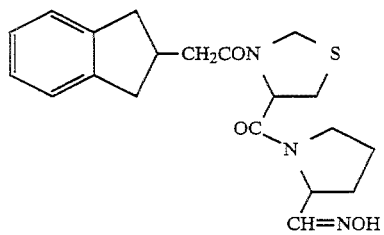

1-[3-(Indan-2-ylacetyl)-L-thioprolyl]-L-prolinal (372 mg), hydroxylamine hydrochloride salt (76 mg) and pyridine (89 μl) were dissolved in 5 ml of dimethylformamide, and stirred at 70° C. for 1.5 hours. After concentrating the reaction solution under reduced pressure, the resulting residue was dissolved in 30 ml of methylene chloride, washed by saturated aqueous sodium chloride solution, and dried over magnesium sulfate, followed by distillation of the solvent under reduced pressure. The resulting residue was purified by column chromatography to obtain 120 mg of (2S)-1-[3-(indan-2-ylacetyl)-L-thioprolyl]-2-pyrrolidine aldoxime. Yield; 31%.

m.p. 146°~147° C. IR(KBr) cm$^{-1}$: 3250, 3000~2800, 1635, 1405, 740 NMR (CDCl$_3$) δ ppm: 1.80~2.30 (4H, m), 2.50~2.68 (4H, m), 2.80~4.00 (7H,m), 4.46~5.19(4H, m), 6.58~7.54(1H, m), 7.10~7.20(4H, m), 8.49~9.48 (1H, m)

EXAMPLE 15

(2S)-1-[3-(Indan-2-ylacetyl)-L-thioprolyl]-2-cyanopyrrolidine

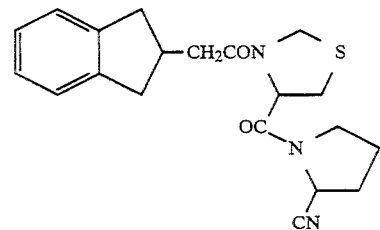

1-[3-(Indan-2-ylacetyl)-L-thioprolyl]-L-prolinal (1.12 g), hydroxylamine hydrochloride salt (229 mg) and pyridine (266 μl) were dissolved in 10 ml of dimethylformamide, and stirred at 70° C. for 1.5 hours to obtain (2S)-1-[3-(indan-2-ylacetyl)-L-thioprolyl]-2-pyrrolidine aldoxime. Subsequently, 366 mg of selenium dioxide was added to the reaction solution, followed by agitation at 70° C. for 3 hours. The residue of selenium dioxide was filtered under aspiration, and the resulting filtrate was concentrated under reduced pressure. The residue was dissolved in 50 ml of methylene chloride, washed sequentially in 1N hydrochloric acid, saturated aqueous sodium chloride solution, and saturated aqueous sodium chloride solution, and dried over magnesium sulfate, followed by distillation of the solvent under reduced pressure. The resulting residue was purified by column chromatography to obtain 278 mg of (2S)-1-[3-(indan-2-yl-acetyl)-L-thioprolyl]-2-cyanopyrrolidine. Yield; 25%.

m.p. 99°~100° C. IR(KBr) cm$^{-1}$: 3600~3200, 3000~2800, 2230, 1655, 1405 NMR (CDCl$_3$) δ ppm: 2.10~2.30(4H, m), 2.52~2.68 (4H, m), 2.87~2.97 (1H, m), 3.10~3.35 (4H, m), 3.60~3.70(1H, m), 3.85~3.95 (1H, m), 4.60~4.67 (2H, m), 4.75~4.85 (1H, m), 4.93 (1H, t, J=7Hz), 7.11~7.20 (4H, m)

EXAMPLE 16

(2S)-1-[3-((S)-1,2,3,4-Tetrahydronaphthalen-2-ylacetyl)-L-thioprolyl]-2-pyrrolidine carbaldehyde semicarbazone

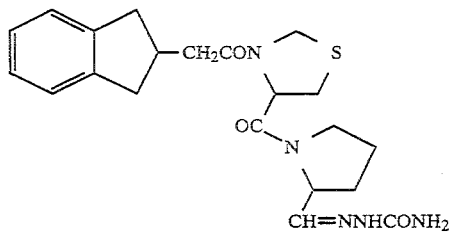

1-[3-(S)-1,2,3,4-Tetrahydronaphthalen-2-ylacetyl)-L-thioprolyl]-L-prolinal (1.02 g), semicarbazide hydrochloride (0.30 g) and sodium acetate (0.22 g) were dissolved in 20 ml of 70% ethanol, and stirred at 80° C. for 10 minutes. The reaction solution was concentrated under reduced pressure, and the residue solution was concentrated under was dissolved in ethyl acetate, washed in water, dried over anhydrous magnesium sulfate, followed by distillation of the solvent under reduced pressure. The resulting residue was purified by column chromatography to obtain 0.56 g of (2S)-1-[3-((S)-1,2,3,4-tetrahydronaphthalen-2-ylacetyl)-L-thioprolyl]-2-pyrrolidine carbaldehyde semicarbazone. Yield; 48%.

m.p. 88°~91° C. IR(KBr) cm$^{-1}$: 3500~2800, 1730~1550, 1400, 740 NMR (CDCl$_3$) δ ppm: 1.40~1.56(1H, m), 1.85~2.10 (5H, m), 2.15~2.55(4H, m), 2.74~3.00(3H, m), 3.02~3.38(2H, m), 3.42~3.93 (2H, m), 4.46~4.73 (3H, m), 5.10(1H, t, J=7Hz), 5.40~5.80(1H, b), 7.00~7.15(4H, m), 9.41~9.13 (1H, m)

EXAMPLE 17

(2S)-1-[1-((S)-1,2,3,4-Tetrahydronaphthalen-2-ylacetyl)-L-proplyl]-2-pyrrolidine carbaldehyde dimethyl acetal

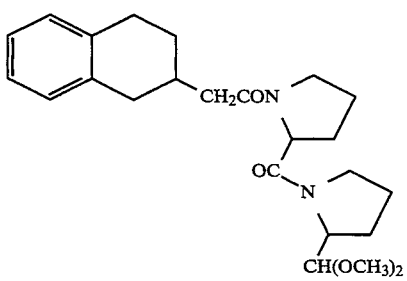

1-[3-((S)-1,2,3,4-Tetrahydronaphthalene-2-ylacetyl)-L-prolyl]-L-prolinal (1.2 g) was dissolved in 10 ml of methanol, and stirred at room temperature for 10 minutes, followed by distillation of the solvent under reduced pressure. The resulting residue was crystallized in ethyl acetate to obtain 1.0 g of (2S)-1-[1-((S)-1,2,3,4-tetrahydronaphthalene-2-yl-acetyl)-L-prolyl]-2-pyrrolidine carbaldehyde dimethyl acetal. Yield; 76%.

m.p. 103°~106° C. IR(KBr) cm$^{-1}$: 3600~3200, 3000~2800, 1630, 1420, 750 NMR (CDCl$_3$) δ ppm: 1.40~1.55(1H, m), 1.80~2.53 (13H, m), 2.72~3.00 (3H, m), 3.39 (3H, s), 3.43 (3H, s), 6.95~7.10 (4H. m)

EXAMPLES 18–28

Following the same method as in Example 2, 13, 14 or 15, the compounds shown in Table 2 were obtained.

The names of the individual compounds are as follows.

EXAMPLE 18

3-[1-(Indan-2-ylacetyl)-L-prolyl]-L-thioprolinol.

EXAMPLE 19

1-[3-((S)-1,2,3,4-Tetrahydronaphthalen-2-ylacetyl)-L-thioprolyl]-L-prolinol.

EXAMPLE 20

1-[3-(Indan-2-ylacetyl)-L-thioprolyl]-L-prolinal.

EXAMPLE 21

3-[1-(Indan-2-ylacetyl)-L-prolyl]-L-thioprolinal.

EXAMPLE 22

1-[3-((S)-1,2,3,4-Tetrahydronaphthalen-2-ylacetyl)-L-thioprolyl]-L-prolinal (m.p. 103°~104° C.).

EXAMPLE 23

(2S)-1-[1-(Indan-2-ylacetyl)-L-prolyl]-2-pyrrolidine aldoxime (m.p. 144°~145° C.).

EXAMPLE 24

(2S)-1-[1-((S)-1,2,3,4-Tetrahydronaphthalen-2-ylacetyl)-L-prolyl]-2-pyprolidine aldoxime (m.p. 170°~171° C.).

EXAMPLE 25

(2S)-1-[3-((S)-1,2,3,4-Tetrahydronaphthalen-2-ylacetyl)-L-thioprolyl]-2-pyrrolidine aldoxime (m.p. 184°~186° C.).

EXAMPLE 26

(2S)-1-[1-(Indan-2-ylacetyl)-L-prolyl]-2-cyanopyrrolidine.

EXAMPLE 27

(2S)-1-[1-((S)-1,2,3,4-Tetrahydronaphthalen-2-ylacetyl)-L-prolyl]-2-cyanopyrrolidine (m.p. 100°~101° C.).

EXAMPLE 28

(2S)-1-[3-((S)-1,2,3,4-Tetrahydronaphthalen-2-ylacetyl)-L-thioprolyl]-2-cyanopyprolidine (m.p. 126°~127° C.).

TABLE 2

Arylalkanoylamine Derivatives [Formula (I)]

| Ex. No. | A | m | X | Y | Z | Yield (%) | IR (cm$^{-1}$) | NMR (δppm) |
|---|---|---|---|---|---|---|---|---|
| 18 | indan-2-yl | 1 | CH$_2$ | S | CH$_2$OH | 42 | (neat): 3600–3100, 3000–2800, 1620, 1420, 740 | (CDCl$_3$): 1.88–2.25(4H, m), 2.38–2.71(4H, m), 2.82–2.99(2H, m), 3.11–3.27(3H, m), 3.46–4.05(4H, m), 4.37–5.11(5H, m), 7.10–7.22(4H, m) |
| 19 | tetrahydronaphthalen-2-yl | 1 | S | CH$_2$ | CH$_2$OH | 78 | (neat): 3650–3100, 3000–2800, 1625, 1410, 740 | (CDCl$_3$): 1.43–2.10(6H, m), 2.30–2.55(4H, m), 2.80–4.40(10H, m), 4.43–4.90(3H, m), 5.08 & 5.42(total 1H, each t, J=7Hz), 7.02–7.20(4H, m) |
| 20 | indan-2-yl | 1 | S | CH$_2$ | CHO | 65 | (KBr): 3650–3100, 3000–2800, 1730, 1640, 1410, 740 | (CDCl$_3$): 1.90–2.16(4H, m), 2.50–2.68(4H, m), 2.89–2.99(1H, m), 3.11–3.44(4H, m), 3.57–3.65(1H, m), 3.90–3.99(1H, m), 4.59–4.66(3H, m), 5.08(1H, t, J=7Hz), 7.10–7.20 (4H, m), 9.52(1H, d, J=1Hz) |
| 21 | indan-2-yl | 1 | CH$_2$ | S | CHO | 60 | (KBr): 3650–3100, 3000–2800, 1730, 1630, 1410, 740 | (CDCl$_3$): 1.90–2.30(4H, m), 2.39–2.70(4H, m), 2.89–3.00(1H, m), 3.11–3.25(4H, m), 3.48–3.65(2H, m), 4.53–4.74(2H, m), 4.98–5.12(2H, m), 7.09–7.19(4H, m), 9.48(1H, s) |
| 22 | tetrahydronaphthalen-2-yl | 1 | S | CH$_2$ | CHO | 87 | (KBr): 3000–2800, 1725, 1640, 1410, 740 | (CDCl$_3$): 1.40–1.57(1H, m), 1.85–2.20(5H, m), 2.30–2.56(4H, m), 2.76–3.02(3H, m), 3.23(1H, dd, J=8Hz, 11Hz), 3.39(1H, dd, J=8Hz, 11Hz), 3.50–3.72(1H, m), 3.90–4.02 (1H, m), 4.60–4.72(3H, m), 5.11(1H, t, J=8Hz), 7.00–7.15(4H, m), 9.54(1H, d, J=2Hz) |

TABLE 2-continued

Arylalkanoylamine Derivatives [Formula (I)]

| Ex. No. | A | m | X | Y | Z | Yield (%) | IR (cm$^{-1}$) | NMR (δppm) |
|---|---|---|---|---|---|---|---|---|
| 23 | indanyl | 1 | $CH_2$ | $CH_2$ | CH=NOH | 21 | (KBr): 3600–3100, 3000–2800, 1620, 1430, 740 | (CDCl$_3$): 1.83–2.27(8H, m), 2.34–2.71(4H, m), 2.88–3.01(1H, m), 3.07–3.22(2H, m), 3.44–3.97(4H, m), 4.31–5.13(2H, m), 6.58–7.59(1H, m), 7.09–7.21(4H, m), 8.74–9.75 (1H, m) |
| 24 | tetrahydronaphthyl | 1 | $CH_2$ | $CH_2$ | CH=NOH | 65 | (KBr): 3300–3000, 3000–2800, 1630, 1420, 750 | (CDCl$_3$): 1.35–1.58(1H, m), 1.82–2.50(13H, m), 2.70–3.00(3H, m), 3.41–3.99(4H, m), 4.35–5.15(2H, m), 6.58–7.60(1H, m), 6.95–7.10(4H, m), 7.80–8.74(1H, m) |
| 25 | tetrahydronaphthyl | 1 | S | $CH_2$ | CH=NOH | 53 | (KBr): 3250, 3000–2900, 1630, 1400, 760 | (CDCl$_3$): 1.61–1.58(1H, m), 1.85–2.10(5H, m), 2.20–2.56(4H, m), 2.73–3.05(3H, m), 3.08–3.45(2H, m), 3.50–4.08(2H, m), 4.64–4.76(2H, m), 4.81–5.28(2H, m), 6.60–7.68 (1H, m), 7.00–7.15(4H, m), 7.80–8.05(1H, b) |
| 26 | indanyl | 1 | $CH_2$ | $CH_2$ | CN | 35 | (neat): 3600–3200, 3000–2800, 1630, 1420, 740 | (CDCl$_3$): 1.86–2.31(8H, m), 2.38–2.70(4H, m), 2.88–2.98(1H, m), 3.10–3.22(2H, m), 3.44–3.89(4H, m), 4.57–4.61(1H, m), 4.82–4.84(1H, m), 7.09–7.18(4H, m) |
| 27 | tetrahydronaphthyl | 1 | $CH_2$ | $CH_2$ | CN | 31 | (KBr): 3600–3300, 3000–2800, 2300, 1660, 1625, 1410 | (CDCl$_3$): 1.43–1.54(1H, m), 1.88–2.53(13H, m), 2.80–2.96(3H, m), 3.49–3.91(4H, m), 4.58–4.63(1H, m), 4.80–4.83(1H, m), 7.03–7.09(4H, m) |
| 28 | tetrahydronaphthyl | 1 | S | $CH_2$ | CN | 17 | (KBr): 3100–2800, 2450, 2230, 1650, 1410, 1210 | (CDCl$_3$): 1.40–1.54(1H m), 1.95–2.05(1H, m), 2.18–2.56(8H, m), 2.80–2.98(3H, m), 3.22(1H, dd, J=7Hz, 12Hz), 3.33(1H, dd, J=7Hz, 12Hz), 3.60–3.70(1H, m), 3.86–3.98 (1H, m), 4.67–4.70(2H, m), 4.81–4.86(1H, m), 4.94(1H, t, J=7Hz), 7.00–7.15(4H, m) |

Test Example 1 (Inhibitory activity against prolyl endopeptidase from brain)

A prolyl endopeptidase was prepared from canine brains according to the method of Yoshimoto et al. [J. Biochem., 94, 325 (1983)].

Following buffer solutions A and B were used for the measurement.

Buffer A: 20 mM Tris-HCl buffer (pH 7.0)
Buffer B: Buffer A containing 0.1% gelatin, 1 mM EDTA, 1 mM 2-mercaptoethanol.

Dilution of the prolyl endopeptidase preparation with Buffer B to a concentration of 0.4 units/ml was done, and the resulting solution was defined as enzyme solution. To 940 μl of Buffer A was added 50 μl of the enzyme solution, followed by incubating at 37° C. for 10 minutes, to which was added 10 μl of a solution of a sample compound dissolved in dimethyl sulfoxide, and stirred and mixed together, followed by staying at 37° C. for ten minutes. To the mixture was added 100 μl of carbobenzoxyglycylprolyl p-nitroanilide dissolved in 40% dioxane to a final concentration of 2.5 mM, for reaction at 37° C. for 10 minutes, to which was added 100 μl of 50% acetic acid containing 10% Triton X-100, thereby terminating the reaction.

For controls, dimethyl sulfoxide was added at the same amount (10 μl) instead of the solution of the sample compound; for blind tests, dimethyl sulfoxide and Buffer B were added instead of a sample compound and the enzyme solution, respectively, at the same amounts for effecting the same procedure.

Absorbance at 410 nm was measured with a spectrophotometer, and the values obtained by subtracting the value from the blind test from the individual values ware defined as enzyme activity.

The prolyl endopeptidase inhibition potency (IC$_{50}$ value) was determined as the concentration (M) of an individual compound inhibiting 50% of the enzyme activity of the control. The results are shown in Table 3.

TABLE 3

| Compounds | Inhibition Potency IC$_{50}$ (M) |
|---|---|
| Compound of Example 2 | 1.0 × 10$^{-9}$ |
| Compound of Example 8 | 1.2 × 10$^{-9}$ |
| Compound of Example 9 | 3.5 × 10$^{-10}$ |
| Compound of Example 10 | 1.4 × 10$^{-9}$ |
| Compound of Example 11 | 6.9 × 10$^{-8}$ |
| Compound of Example 25 | 1.6 × 10$^{-8}$ |
| Compound of Example 28 | 7.5 × 10$^{-10}$ |
| Aniracetam | >1.0 × 10$^{-3}$ |
| SUAM 1221[a] | 7.6 × 10$^{-8}$ |

[a] Compound disclosed in Japanese Patent Unexamined Publication No. 62-201877.

Test Example 2 (Anti-hypoxic activity)

Groups of ICR male mice (Charles River Co.), age 4 to 5 weeks, each group consisting of 10 mice and each mouse having been fasted for 24 hours, were used for the test. Mice were placed in a transparent desiccator (diameter: 19 cm, height: 30 cm) made of synthetic resin and having 2 valves, one at the upper portion and the other at the lower portion, for replacing the gas therein. A mixed gas containing 4% O$_2$ and 96% N$_2$ was fed from the upper valve at a rate of 10 l/min to measure the period of time until respiratory arrest took place for each mouse. The time measured was taken as the survival time.

Each tested compound suspended in an solvent was intraperitoneally administered 30 minutes before the start of the mixed gas feeding. A group of mice to which only the solvent was intraperitoneally administered was used as a control.

The anti-hypoxic activity was determined according to the following equation:

$$\text{Anti-hypoxic Activity (\%)} = \frac{\text{Survival time of the group to which a test compound was administered}}{\text{Survival time of the control group}} \times 100$$

The results are shown in Table 4.

TABLE 4

| Compounds | Dose (mg/kg) | Anti-hypoxic Activity (%) |
| --- | --- | --- |
| Control | — | 100 |
| Compound of Example 2 | 100 | 120 |
| Compound of Example 5 | 100 | 115 |
| Compound of Example 6 | 100 | 128 |
| Compound of Example 8 | 100 | 120 |
| Compound of Example 9 | 100 | 123 |
| Compound of Example 10 | 100 | 129 |
| Aniracetam | 100 | 115 |

As shown in Tables 3 and 4, the compounds (I) of the present invention are superior to aniracetam and SUAM 1221 (the compound described in Japanese Patent Unexamined Publication No. 62-201877, in their prolyl endopeptidase inhibitory activities against the prolyl endopeptidase from canine brain and anti-hypoxic activities.

Test Example 3 (Resistance to amnesia)

The action of the compound of the present invention on the inhibition of prolonged memory retention via an amnesia-inducing agent cyclohexyimide.

Male ICR mice (Charles River, Co. Ltd.), aged 0 to 7 weeks, were employed for this test with a step-down passive avoidance system.

On day 1, the mice were placed on a rubber-made platform, for 5-minute learning trial. Whenever the mice got down on the grid floor, 0.2-mA electric shock was continuously given to the mice until the mice got on the platform.

The administration of cyclohexyimide and a sample compound was done immediately after the termination of the learning trial. Cyclohexyimide was dissolved in physiological saline and subcutaneously administered at a dose of 150 mg/kg, while the compound of the present invention (Example 22) was suspended in 10% gum arabic for parenteral administration at a dose of 30 µg/kg.

Twenty-four hours after the learning trial, retention test was performed. The mice were again placed on the platform, and the potential time required until the mice got down from the platform was counted. The ratio of the amnesic mice with the potential time less than 100 seconds per dose group was calculated, and the results are shown in FIG. 1. The significance was tested by $\chi^2$-test, by using a level of significance (p) obtained by the comparative results with a group with a dose of cyclohexyimide+solvent (*p<0.05, **p<0.01).

As a result, the amnesic ratio of the group with the dosage of cyclohexyimide alone was 71.4%, whereas the amnesic ratio of the group with the dosage of the compound of the present invention was 36.8%, which indicates that the compound of the present invention exhibits great resistance to amnesia.

Test Example 4 (Toxicity test; Parenteral administration)

Ten ICR mice (Charles River, Co.), male, aged 4 to 5 weeks, were employed per group. The compounds of Examples 1, 5, 8 and 12 were separately suspended in 10% gum arabic, and then, they were individually administered parenterally at a dose of 300 mg/kg for subsequent observation for 7 days. As a result, no death was counted under the above conditions.

Test Example 5 (Toxicity test; Oral administration)

Five male ICR mice (Charles River, Co.) of age 5 weeks, were employed per group. The compound of Example 22 was suspended in a solvent, which was then administered orally at a dose of 1,000 mg/kg for subsequent observation for 7 days. As a result, no death was counted under the above conditions.

Preparation Example 1

| Compound of Example 5 | 50 g |
| --- | --- |
| Lactose | 315 g |
| Corn starch | 125 g |
| Crystalline cellulose | 25 g |

The above components were uniformly mixed together, to which was added 200 ml of an aqueous 7.5% hydroxypropyl cellulose solution. The resulting mixture was prepared into granule with an extrusion granulator, by using a screen of a 0.5-mm diameter, which were immediately rounded with a marumerizor, followed by drying to prepare granules.

By means of a fluid-bed granulator, the dry granules were coated with 1.9 kg of a film coating solution of the following composition to prepare enteric granules.

| Composition of coating solution: | | |
| --- | --- | --- |
| Hydroxypropylmethyl cellulose phthalate | 5.0 | (w/w) % |
| Stearic acid | 0.25 | (w/w) % |
| Methylene chloride | 50.0 | (w/w) % |
| Ethanol | 44.75 | (w/w) % |

Preparation Example 2

| Compound of Example 10 | 20 g |
| --- | --- |
| Lactose | 100 g |
| Corn starch | 36 g |
| Crystalline cellulose | 30 g |
| Carboxymethyl cellulose calcium | 10 g |
| Magnesium stearate | 4 g |

The components of the above composition were uniformly mixed together, to prepare tables, each of 200 mg, by means of a single-punch tablet machine using a punch of a 7.5-mm diameter.

Next, the tablets were subjected to spray coating with a coating solution of the following composition, thereby providing 10-mg coating per tablet, to prepare enteric film-coating tablets.

| Composition of coating solution: | | |
| --- | --- | --- |
| Hydroxypropylmethyl cellulose phthalate | 8.0 | (w/w) % |

-continued

| Composition of coating solution: | | |
|---|---|---|
| Glycerin fatty acid ester | 0.4 | (w/w) % |
| Methylene chloride | 50.0 | (w/w) % |
| White beewax | 0.1 | |
| Isopropanol | 41.5 | (w/ |

Industrial Applicability

Because the compound of the present invention has the prolyl endopeptidase inhibitory action and the resistances to hypoxia and amnesia, the compound concurrently has both of the actions for improving mneme and for improving cerebral circulation and cerebral metabolism, and also is of higher safety. Thus, the compound of the present invention is useful as therapeutic drugs for sequelae of brain hemorrhage, brain infarct, cerebral aorta sclerosis, subarachnoid hemorrhage, head injury, brain surgery, cerebrovascular dementia, Parkinson disease, Altzheimer disease, Peck disease, sequela of hypoxia toxicity, alcoholic encephalopathia, and the like.

What is claimed is:

1. An arylalkanoylamine derivative represented by the following general formula (I):

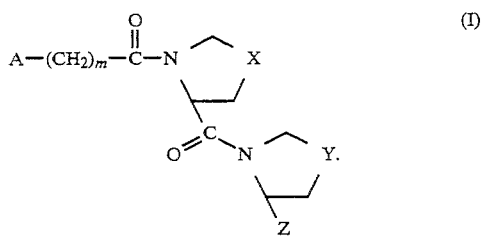

wherein A represents an indanyl, indenyl, 1,2,3,4-tetrahydronaphthalenyl or benzofuranyl group; m represents an integer of 0 to 5; Z represents a nitrile, hydroxyiminomethyl or semicarbazonomethyl group; X and Y may be the same or different, and individually represent a methylene group or sulfur atom.

2. The arylalkanoylamine derivative of claim 1 wherein A represents an indanyl or 1,2,3,4-tetrahydronaphthalenyl group; and Z represents a nitrile group.

3. The arylalkanoylamine derivative selected from the group consisting of
   (2S)-1-[3-((S)-1,2,3,4-tetrahydronaphthalen-2-ylacetyl)-L-thioprolyl]-2-pyrrolidine aldoxime; and
   (2S)-1-[3-((S)-1,2,3,4-tetrahydronaphthalen-2-ylacetyl)-L-thioprolyl]-2-cyanopyrrolidine.

4. The arylalkanoylamine derivative (2S)-1-[3-((S)-1,2,3,4-tetrahydronaphthalen-2-ylacetyl)-L-thioprolyl]-2-cyanopyrrolidine.

5. A pharmaceutical composition for improving mneme, cerebral circulation and cerebral metabolism comprising an effective amount of the arylalkanoylamine derivative of claim 1 and a pharmaceutically acceptable carrier.

6. A pharmaceutical composition for improving mneme, cerebral circulation and cerebral metabolism comprising an effective amount of the arylalkanoylamine derivative of claim 2 and a pharmaceutically acceptable carrier.

7. A pharmaceutical composition for improving mneme, cerebral circulation and cerebral metabolism comprising an effective amount of the arylalkanoylamine derivative of claim 3 and a pharmaceutically acceptable carrier.

8. A pharmaceutical composition for improving mneme, cerebral circulation and cerebral metabolism comprising an effective amount of the arylalkanoylamine derivative of claim 4 and a pharmaceutically acceptable carrier.

9. A method for treating senile dementia comprising administering to a subject an effective amount of the pharmaceutical composition of claim 5.

10. A method for treating senile dementia comprising administering to a subject an effective amount of the pharmaceutical composition of claim 6.

11. A method for treating senile dementia comprising administering to a subject an effective amount of the pharmaceutical composition of claim 7.

12. A method for treating senile dementia comprising administering to a subject an effective amount of the pharmaceutical composition of claim 8.

* * * * *